US012698254B2

(12) United States Patent
Albaneze-Walker

(10) Patent No.: US 12,698,254 B2
(45) Date of Patent: Aug. 4, 2026

(54) CRYSTALLINE SOLIDS OF 3-PALMITOYL-AMIDO-1,2-PROPANEDIOL AND 3-PALMITOYL-AMIDO-2-HYDROXY-1-DIMETHOXYTRIPHENYLMETHYLETHER-PROPANE AND METHODS OF MAKING AND USING THE SAME

(71) Applicant: Geron Corporation, Foster City, CA (US)

(72) Inventor: Jennifer E. Albaneze-Walker, Foster City, CA (US)

(73) Assignee: Geron Corporation, Foster City, CA (US)

( * ) Notice: Subject to any disclaimer, the term of this patent is extended or adjusted under 35 U.S.C. 154(b) by 0 days.

(21) Appl. No.: 18/635,809

(22) Filed: Apr. 15, 2024

(65) Prior Publication Data

US 2024/0360074 A1 Oct. 31, 2024

Related U.S. Application Data

(62) Division of application No. 17/079,204, filed on Oct. 23, 2020, now Pat. No. 11,987,540.

(60) Provisional application No. 62/926,810, filed on Oct. 28, 2019.

(51) Int. Cl.
*C07C 233/18* (2006.01)
*B01D 9/00* (2006.01)
*C07C 231/24* (2006.01)

(52) U.S. Cl.
CPC .......... *C07C 233/18* (2013.01); *B01D 9/0031* (2013.01); *B01D 2009/0086* (2013.01); *C07B 2200/13* (2013.01); *C07C 231/24* (2013.01)

(58) Field of Classification Search
None
See application file for complete search history.

(56) References Cited

U.S. PATENT DOCUMENTS

| | | | | |
|---|---|---|---|---|
| 9,266,816 | B2 | 2/2016 | Shrawat et al. | |
| 9,657,296 | B2 | 5/2017 | Gryaznov et al. | |
| 2006/0069156 | A1 | 3/2006 | Darteil et al. | |
| 2006/0121583 | A1 | 6/2006 | Lassalle et al. | |
| 2006/0154984 | A1 | 7/2006 | Darteil et al. | |
| 2009/0048427 | A1 | 2/2009 | Hedgpeth et al. | |
| 2011/0286937 | A1 | 11/2011 | Kiso et al. | |
| 2012/0329858 | A1* | 12/2012 | Gryaznov | C12N 15/1137 435/375 |
| 2015/0337314 | A1 | 11/2015 | Premchandran | |
| 2017/0130225 | A1 | 5/2017 | Gryaznov et al. | |

FOREIGN PATENT DOCUMENTS

| | | |
|---|---|---|
| CN | 106459134 | 2/2017 |
| EP | 1644318 | 5/2008 |
| KR | 101809614 | 12/2017 |
| KR | 101861785 | 5/2018 |
| WO | WO9518820 | 7/1995 |
| WO | WO1996032496 A2 | 10/1996 |
| WO | WO2005023994 | 3/2005 |
| WO | WO2019011829 A1 | 1/2019 |

OTHER PUBLICATIONS

Gehlert et al., (1998) "Relating Domain Morphology and Lattice Structure in Monolayers of Glycerol Amide Lipids", Langmuir, 14(8): 2112-2118.
Pubchem-CID: 11002017 Create Date: Oct. 26, 2006 (Oct. 26, 2006) pp. 1-11; p. 2.
Ouyang et al., "Structure—Activity Relationship for Enhancement of Paracellular Permeability across Cacom2 Cell Monolayers by 3mA1kylamidom2malkoxypropylphosphocholines" (2002) J. Med. Chem., 45: 2857-2866.
Xu et al. (2016) "Quantitative chemical analysis", Nankai University Press, 2 pages.
Legrand et al., (2016) "Hybrid Fluorinated and Hydrogenated Double-Chain Surfactants for Handling Membrane Proteins", The Journal of Organic Chemistry, 81(2):681-688.
Liang, (2007) "Screening Polymorphic Forms of Drug substances by Using Generalized Crystallization Techniques", National Taipei University of Technology, Chemical Engineering, pp. 1-149.
Asahara, (1985) "Handbook of solvent", Kodansha Ltd., p. 47-51.
Hirayama, (2008) "Handbook for preparation of organic compound crystal-principle and know how", pp. 57-84.
Maruzen, (2003) "technique of chemical synthesis", The Chemical Society of Japan, Handbook of chemistry, applied chemistry, 6(4):178.
Matsuoka, (2010) "Base & Application of Polymorphic Crystals", popular edition, 1st printing, CMC Publishing Co., Ltd., pp. 105-117, 181-191.
Marx et.al., (1988) "Synthesis and evaluation of neoplastic cell growth inhibition of 1-N-alkylamide analogs of glycero-3-phosphocholine", Journal of Medicinal Chemistry, 31:858-863.
Takata, (2007) "API form screening and selection in drug discovery stage", Pharm Stage, 6(10):20-25.
Wermuth, (1999) "The Practice of Medicinal Chemistry", Technomics, Inc., pp. 347-365, 452-453.

(Continued)

*Primary Examiner* — Renee Claytor
*Assistant Examiner* — Jennifer C Sawyer
(74) *Attorney, Agent, or Firm* — Rudy J. Ng; Travis Young; Bozicevic, Field & Francis LLP

(57) ABSTRACT

Aspects of the disclosure include crystalline solids of 3-palmitoyl-amido-1,2-propanediol and 3-palmitoyl-amido-2-hydroxy-1-dimethoxytriphenylmethylether-propane. Methods for preparing the crystalline solids of 3-palmitoyl-amido-1,2-propanediol and single crystals of 3-palmitoyl-amido-2-hydroxy-1-dimethoxytriphenylmethylether-propane are also provided. Methods for preparing a 3-palmitoyl-amido-2-hydroxy-1-dimethoxytriphenylmethylether-propane from a crystalline solid of 3-palmitoyl-amido-1,2-propanediol are also described.

4 Claims, 8 Drawing Sheets

(56) References Cited

OTHER PUBLICATIONS

Strain, Jacob; (2025) "X-Ray Diffraction (XRD)—XRD Principle, XRD Analysis and Applications" Technology Networks; 1-24.
Haleblian and McCrone, (1969) "Pharmaceutical Applications of Polymorphism", Journal of Pharmaceutical Sciences, 58(8), 911-929.
*Grunenthal GmbH* v. *Alkem Laboratories Limited*, (2019), United States Court of Appeals for the Federal Circuit, 1-23.

* cited by examiner

CRYSTALLINE SOLIDS OF 3-PALMITOYL-AMIDO-1,2-PROPANEDIOL AND 3-PALMITOYL-AMIDO-2-HYDROXY-1-DIMETHOXYTRIPHENYLMETHYLETHER-PROPANE AND METHODS OF MAKING AND USING THE SAME

CROSS-REFERENCE TO RELATED APPLICATIONS

This application is a divisional of U.S. application Ser. No. 17/079,204, filed Oct. 23, 2020, now issued as U.S. Pat. No. 11,987,540, which claims benefit of priority to U.S. Provisional Patent Application Ser. No. 62/926,810 filed Oct. 28, 2019, the disclosures of which are herein incorporated by reference.

INTRODUCTION

Imetelstat is a telomerase inhibitor that binds with high affinity to the template region of the RNA component of telomerase. Studies have shown that imetelstat inhibits telomerase activity and is effective against cell proliferation in a multitude of different cancer cell lines and human tumors. Imetelstat has been used in clinical trials of patients with hematologic malignancies. A clinical trial of patients with myelofibrosis showed that imetelstat was able to achieve complete clinical remissions in certain patients. In these patients, imetelstat led to the reversal of bone marrow fibrosis and resulted in morphologic and molecular remission.

The structure of imetelstat includes a N3'→P5' thiophosphoramidate oligonucleotide. The synthesis of imetelstat has been carried out by solid phase oligonucleotide synthesis where the first phosphoramidite nucleotide is coupled to the support followed by sulfurization. Chain elongation of the oligonucleotide component is achieved by repeated reaction of the 3'-amino group of the solid-phase support bonded oligonucleotide with additional nucleotide phosphoramidite monomers. The oligonucleotide of imetelstat is coupled to the solid phase support through a palmitoyl-amide linker. This fatty acid-amide linker is thus a component in the synthesis of imetelstat.

SUMMARY

Aspects of the disclosure include crystalline solids of 3-palmitoyl-amido-1,2-propanediol (Formula I):

(I)

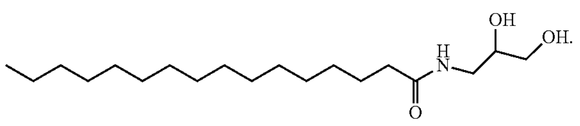

In embodiments, the crystalline solid of 3-palmitoyl-amido-1,2-propanediol has a x-ray powder diffraction (XRPD) pattern that includes a peak at about 8.25° 2Θ. In certain embodiments, the crystalline solid of 3-palmitoyl-amido-1,2-propanediol has a x-ray powder diffraction (XRPD) pattern that includes one or more peaks at about 2.75° 2Θ; about 6° 2Θ; about 3.8° 2Θ; about 15° 2Θ; about 26.3° 2Θ; about 30.5° 2Θ and about 33.10°2Θ. The crystalline solid of 3-palmitoyl-amido-1,2-propanediol is, in some instances, characterized by a single weight loss step by thermogravimetric analysis (TGA). In certain instances, the weight loss step begins at about 200.5° C. In some embodiments, the crystalline solid of 3-palmitoyl-amido-1,2-propanediol exhibits a first endotherm at about 79.3° C. and a second endotherm at about 102.5° C. by differential scanning calorimetry (DSC). In these embodiments, the second endotherm is a single peak endotherm.

Methods for preparing the crystalline solid of 3-palmitoyl-amido-1,2-propanediol are also provided. In practicing methods according to certain embodiments, 3-palmitoyl-amido-1,2-propanediol is contacted with one or more solvents to produce a 3-palmitoyl-amido-1,2-propanediol composition and precipitated to produce a 3-palmitoyl-amido-1,2-propanediol crystalline solid. In some embodiments, 3-palmitoyl-amido-1,2-propanediol is contacted with a polar solvent. In other embodiments, 3-palmitoyl-amido-1,2-propanediol is contacted with a non-polar solvent. In still other embodiments, 3-palmitoyl-amido-1,2-propanediol is contacted with a mixture of a polar solvent and a non-polar solvent. The solvent may further include an organic base, such as triethylamine. In some embodiments, the solvent is selected from tetrahydrofuran, methyltetrahydrofuran, dichloromethane, isopropylacetate, ethyl acetate, 1,2-dichloroethane (DCE), dimethylformamide (DMF), acetone, dimethylacetamide, dimethylsulfoxide (DMSO), acetonitrile, toluene, 2-methylbutan-2-ol (tAmOH) and N-methyl-2-pyrrolidone (NMP) or a combination thereof. In some instances, the solvent is selected from tetrahydrofuran, methyltetrahydrofuran and dichloromethane. In certain instances, the solvent is tetrahydrofuran. In certain embodiments, precipitating the crystalline solid of 3-palmitoyl-amido-1,2-propanediol includes heating the 3-palmitoyl-amido-1,2-propanediol composition to produce a heated composition (e.g., where 3-palmitoyl-amido-1,2-propanediol is solubilized in the solvent) and cooling the heated 3-palmitoyl-amido-1,2-propanediol composition to produce crystalline solids of 3-palmitoyl-amido-1,2-propanediol.

Methods for preparing 3-palmitoyl-amido-2-hydroxy-1-dimethoxytriphenylmethylether-propane from 3-palmitoyl-amido-1,2-propanediol are also described. In practicing the subject methods according to certain embodiments, a solvent is contacted with a crystalline solid of 3-palmitoyl-amido-1,2-propanediol to generate a precursor composition; and the precursor composition is contacted with a composition comprising dimethoxytriphenylmethyl chloride to generate a composition having 3-palmitoyl-amido-2-hydroxy-1-dimethoxytriphenylmethylether-propane. In some embodiments, the solvent is tetrahydrofuran, methyltetrahydrofuran, dichloromethane, isopropylacetate (iPrOAc), ethyl acetate, 1,2-dichloroethane (DCE), dimethylformamide (DMF), acetone, dimethylsulfoxide (DMSO), acetonitrile, toluene, 2-methylbutan-2-ol (tAmOH), N-methyl-2-pyrrolidone (NMP) or a combination thereof. In some instances, the solvent is selected from tetrahydrofuran, methyltetrahydrofuran, dichloromethane, isopropylacetate, acetonitrile, toluene, 2-methylbutan-2-ol (tAmOH) and N-methyl-2-pyrrolidone (NMP). In certain instances, the solvent is selected from methyltetrahydrofuran, tetrahydrofuran and dichloromethane.

In some embodiments, the precursor composition includes a base, such as an organic base. For example, the base may be 1,8-bis(dimethylamino)naphthalene (proton sponge), imidazole, 1,8-diazabicyclo[5.4.0]undec-7-ene (DBU), 2,4,6-trimethylpyridine (collidine), triethylamine (TEA), potassium carbonate, sodium methoxide, tetramethylethylenediamine (TMEDA) or dimethylaminoethanol. In some instances, the base is selected from 1,8-bis(dimethylamino)naphthalene (proton sponge), tetramethylethylenediamine (TMEDA) and triethylamine (TEA). In certain instances, the base is triethylamine.

In other embodiments, the precursor composition includes an additive. For example, the additive may be calcium oxide, magnesium oxide, boric acid, tetra-n-butyl ammonium fluoride (TBAF), 4-dimethylaminopyridine (DMAP), copper chloride ($CuCl_2$), ytterbium (III) chloride ($YbCl_3$) or 1,4-diazabicyclo[2.2.2]octane (DABCO). In some instances, the additive is selected from tetra-n-butyl ammonium fluoride (TBAF), magnesium oxide and boric acid. In certain instances, the additive is magnesium oxide.

In certain instances, the crystalline solid of 3-palmitoyl-amido-1,2-propanediol has a x-ray powder diffraction (XRPD) pattern that includes one or more peaks at about 2.75° 2Θ; about 6° 2Θ; about 3.8° 2Θ; about 8.25° 2Θ; about 15° 2Θ; about 26.3° 2Θ; about 30.5° 2Θ and about 33.1° 2Θ. The crystalline solid of 3-palmitoyl-amido-1,2-propanediol is, in some instances, characterized by a single weight loss step by thermogravimetric analysis (TGA). In certain instances, the weight loss step begins at about 200.5° C. In some embodiments, the crystalline solid of 3-palmitoyl-amido-1,2-propanediol exhibits a first endotherm at about 79.3° C. and a second endotherm at about 102.5° C. by differential scanning calorimetry (DSC).

In some instances, methods further include forming (e.g., by recrystallization) one or more single crystals of 3-palmitoyl-amido-2-hydroxy-1-dimethoxytriphenylmethylether-propane. In these embodiments, 3-palmitoyl-amido-2-hydroxy-1-dimethoxytriphenylmethylether-propane is contacted with a solvent and the crystalline solid of 3-palmitoyl-amido-2-hydroxy-1-dimethoxytriphenylmethylether-propane is precipitated from the solvent. In some instances, the solvent is a polar solvent. In other instances, the solvent is a non-polar solvent. In yet other instances, the solvent is a mixture of a polar solvent and a non-polar solvent. In certain embodiments, forming a crystalline solid of 3-palmitoyl-amido-2-hydroxy-1-dimethoxytriphenylmethylether-propane includes heating the 3-palmitoyl-amido-2-hydroxy-1-dimethoxytriphenylmethylether-propane composition to produce a heated composition and cooling the heated composition to produce a crystalline solid of 3-palmitoyl-amido-2-hydroxy-1-dimethoxytriphenylmethylether-propane, such as one or more single crystals of 3-palmitoyl-amido-2-hydroxy-1-dimethoxytriphenylmethylether-propane.

Aspects of the disclosure also include a crystalline solid of 3-palmitoyl-amido-2-hydroxy-1-dimethoxytriphenylmethylether-propane (Formula II):

each conformation (bent and linear) of 3-palmitoyl-amido-2-hydroxy-1-dimethoxytriphenylmethylether-propane is present in the unit cell in a ratio of 1:1. Each unit cell in the crystalline solid includes 4 molecules of 3-palmitoyl-amido-2-hydroxy-1-dimethoxytriphenylmethylether-propane. In some embodiments, the unit cell has dimensions of about 8.44 Å×about 26.56 Å×about 10.06 Å, where the volume of the unit cell is about 2254.8 $Å^3$. The subject 3-palmitoyl-amido-2-hydroxy-1-dimethoxytriphenylmethylether-propane crystalline solids have a density of from about 1.2 $g/cm^3$ to about 1.3 $g/cm^3$ and have a polymorph purity of 95% or more.

Methods for preparing a crystalline solid of 3-palmitoyl-amido-2-hydroxy-1-dimethoxytriphenylmethylether-propane are also provided. In practicing methods according to certain embodiments, 3-palmitoyl-amido-2-hydroxy-1-dimethoxytriphenylmethylether-propane is contacted with one or more solvents to produce a 3-palmitoyl-amido-2-hydroxy-1-dimethoxytriphenylmethylether-propane composition and precipitated to produce a 3-palmitoyl-amido-2-hydroxy-1-dimethoxytriphenylmethylether-propane crystalline solid, such as one or more single crystals of 3-palmitoyl-amido-2-hydroxy-1-dimethoxytriphenylmethylether-propane. In some embodiments, 3-palmitoyl-amido-2-hydroxy-1-dimethoxytriphenylmethylether-propane is contacted with a polar solvent. In other embodiments, 3-palmitoyl-amido-2-hydroxy-1-dimethoxytriphenylmethylether-propane is contacted with a non-polar solvent. In still other embodiments, 3-palmitoyl-amido-2-hydroxy-1-dimethoxytriphenylmethylether-propane is contacted with a mixture of a polar solvent and a non-polar solvent. In certain instances, the polar solvent is dichloromethane and the non-polar solvent is pentane. In certain embodiments, precipitating the crystalline solid of 3-palmitoyl-amido-2-hydroxy-1-dimethoxytriphenylmethylether-propane includes heating the 3-palmitoyl-amido-2-hydroxy-1-dimethoxytriphenylmethylether-propane composition to produce a heated composition (e.g., where 3-palmitoyl-amido-2-hydroxy-1-dimethoxytriphenylmethylether-propane is solubilized in the solvent) and cooling the heated 3-palmitoyl-amido-2-hydroxy-1-dimethoxytriphenylmethylether-propane composition to produce a crystalline solid of 3-palmitoyl-amido-2-hydroxy-1-dimethoxytriphenylmethylether-propane.

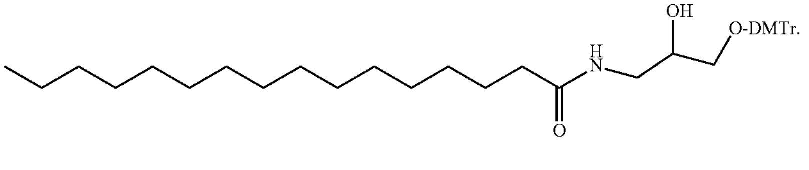

(II)

In certain instances, the crystalline solid of 3-palmitoyl-amido-2-hydroxy-1-dimethoxytriphenylmethylether-propane is a single crystal of 3-palmitoyl-amido-2-hydroxy-1-dimethoxytriphenylmethylether-propane. The crystalline solid, according to embodiments, is in monoclinic crystalline form. Each unit cell in the crystalline solid includes two different conformations of 3-palmitoyl-amido-2-hydroxy-1-dimethoxytriphenylmethylether-propane, such as a bent conformation and a linear conformation. In embodiments, panediol formed from the solutions of (b) THF, (c) 2-methyl THF and (d) DCM and a comparison with the (a) 3-palmitoyl-amido-1,2-propanediol starting material.

Figure 2:
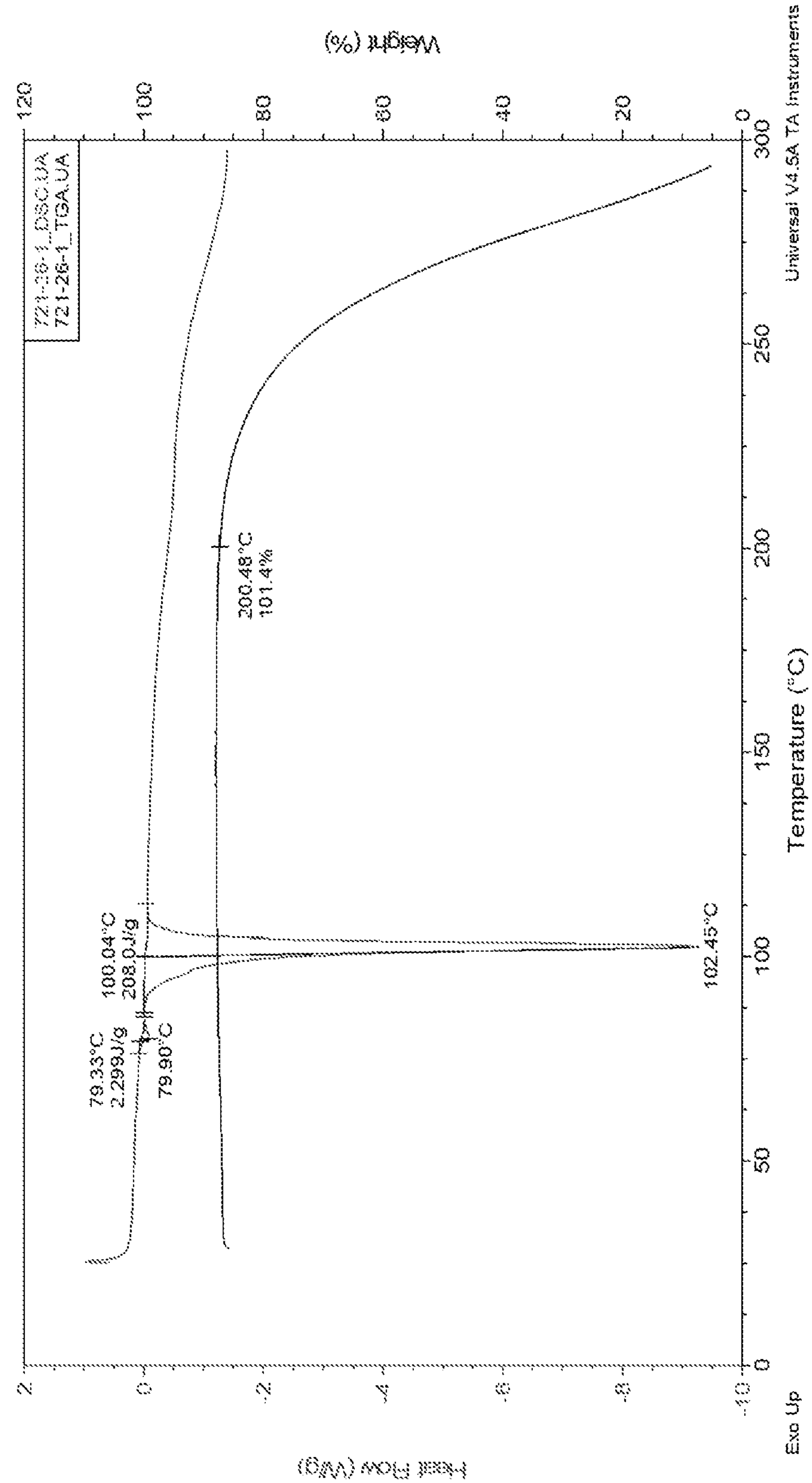

FIG. 2 shows a thermogram from thermogravimetric analysis (TGA) of a polymorphic crystalline solid of 3-palmitoyl-amido-1,2-propanediol formed from solutions of THF according to certain embodiments. The graph in FIG. 2 also depicts the differential scanning calorimetry (DSC) plot of a polymorphic crystalline solid of 3-palmitoyl-amido-1,2-propanediol formed from THF according to certain embodiments.

Figure 3:
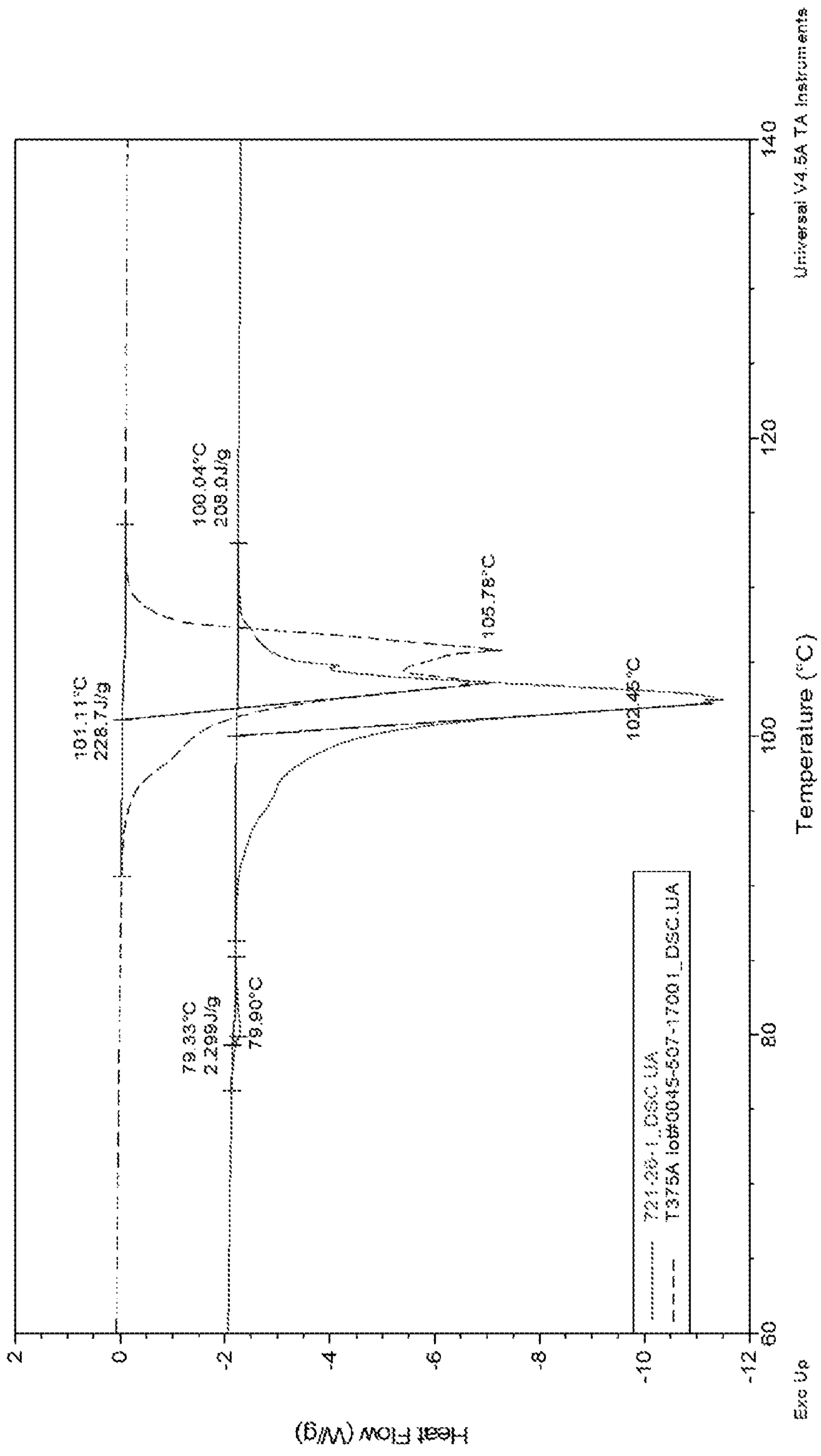

FIG. 3 depicts a comparison of the DSC plot of a polymorphic crystalline solid of 3-palmitoyl-amido-1,2-propanediol formed from THF and the DSC plot of the 3-palmitoyl-amido-1,2-propanediol starting material.

Figure 4A:
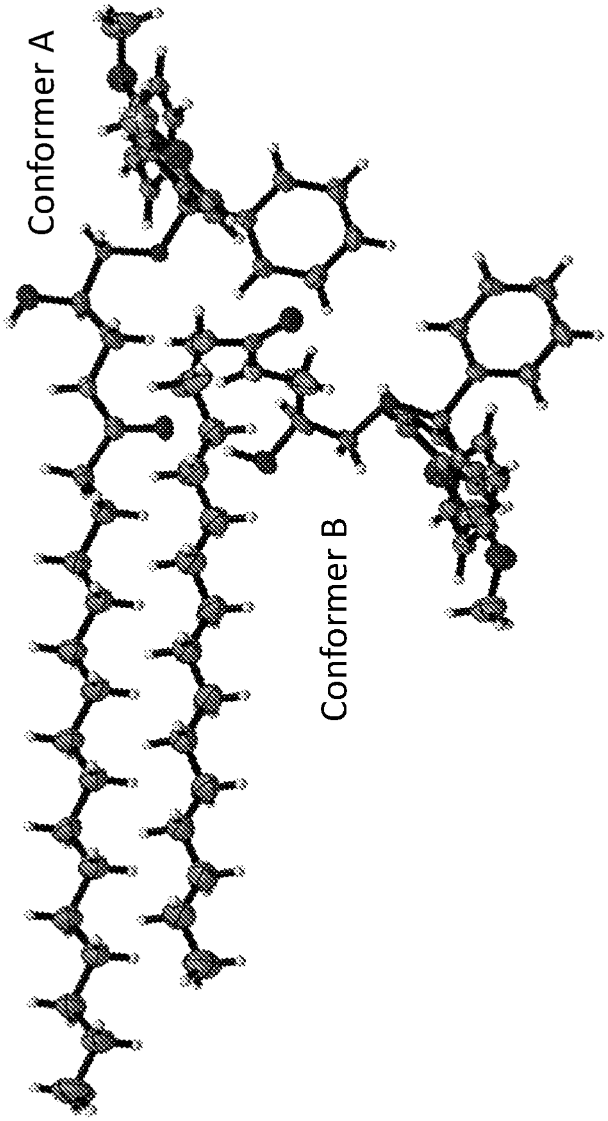
Figure 4B:
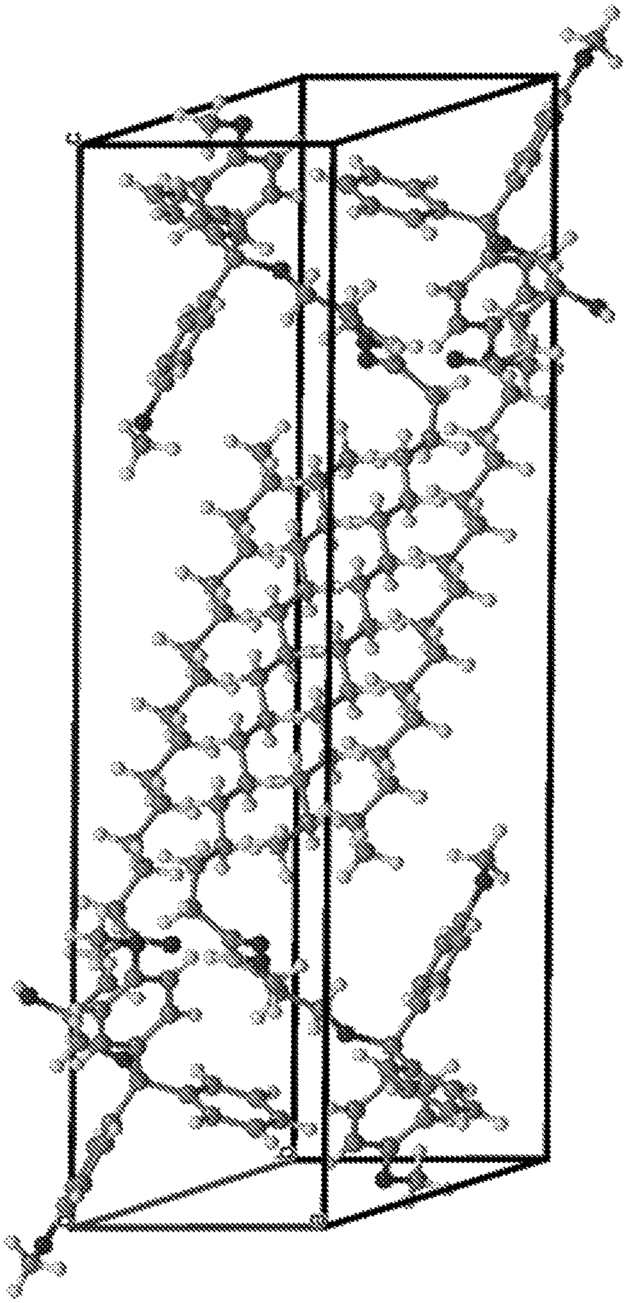
Figure 4C:
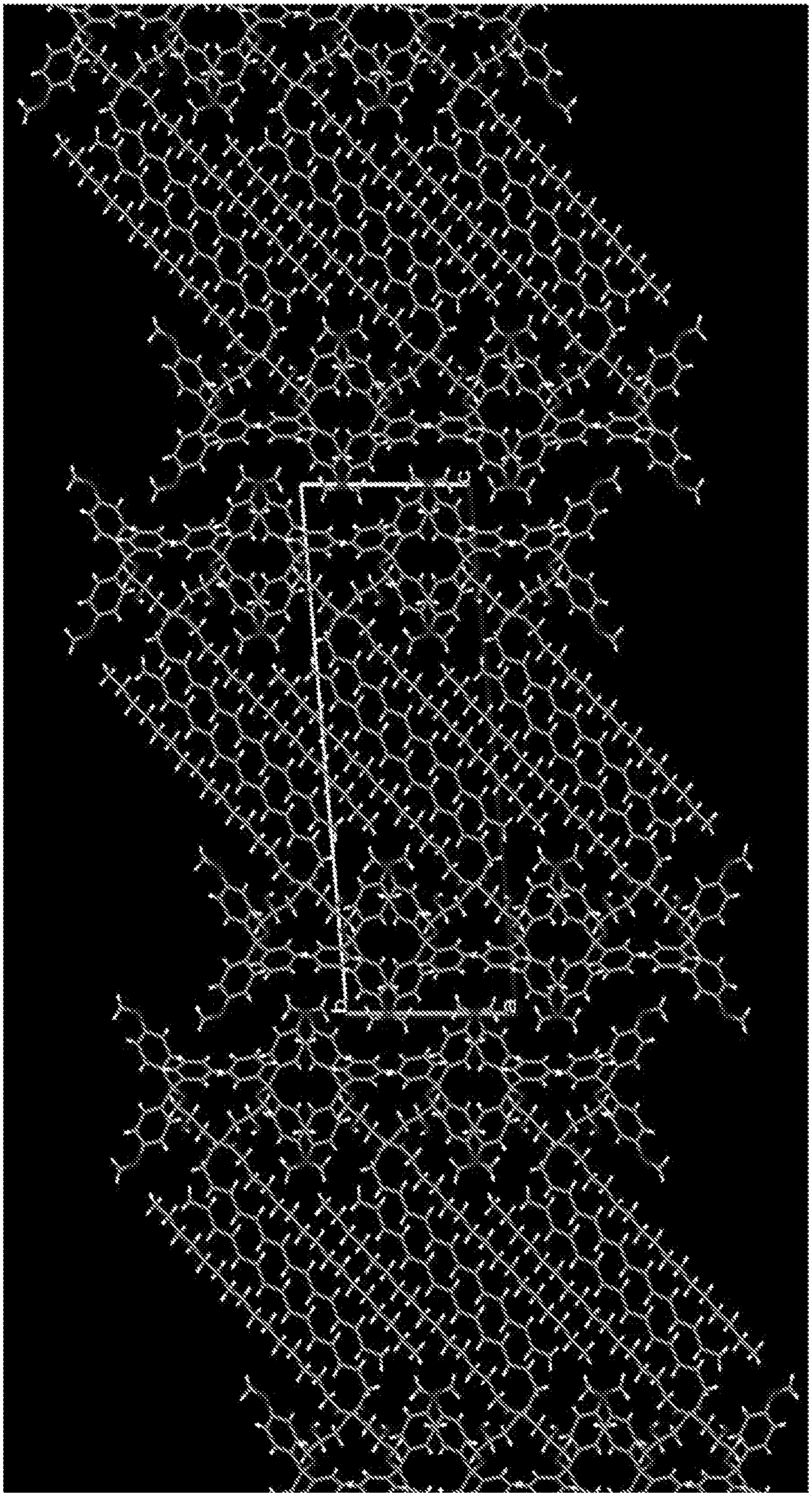
Figure 4D:
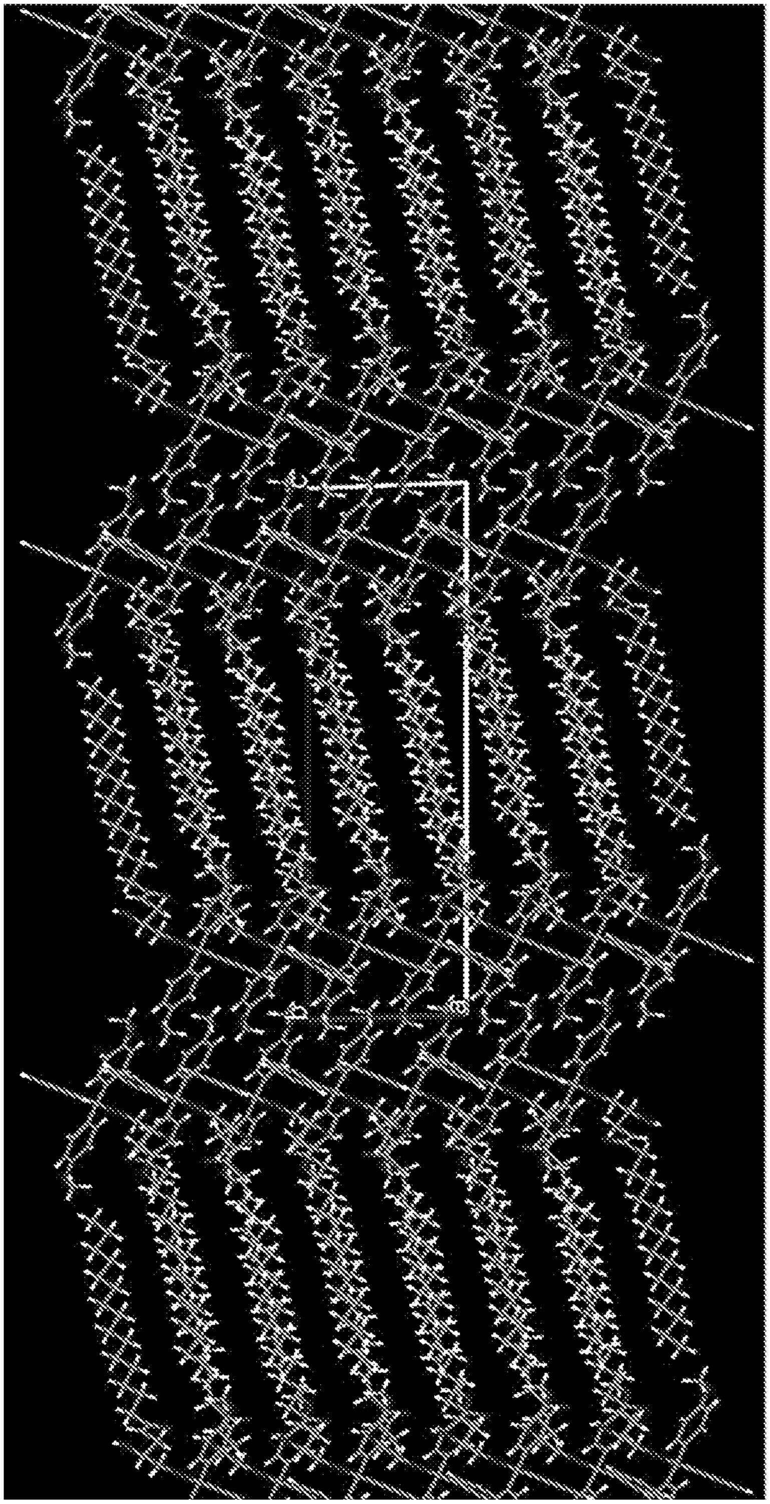
Figure 4E:
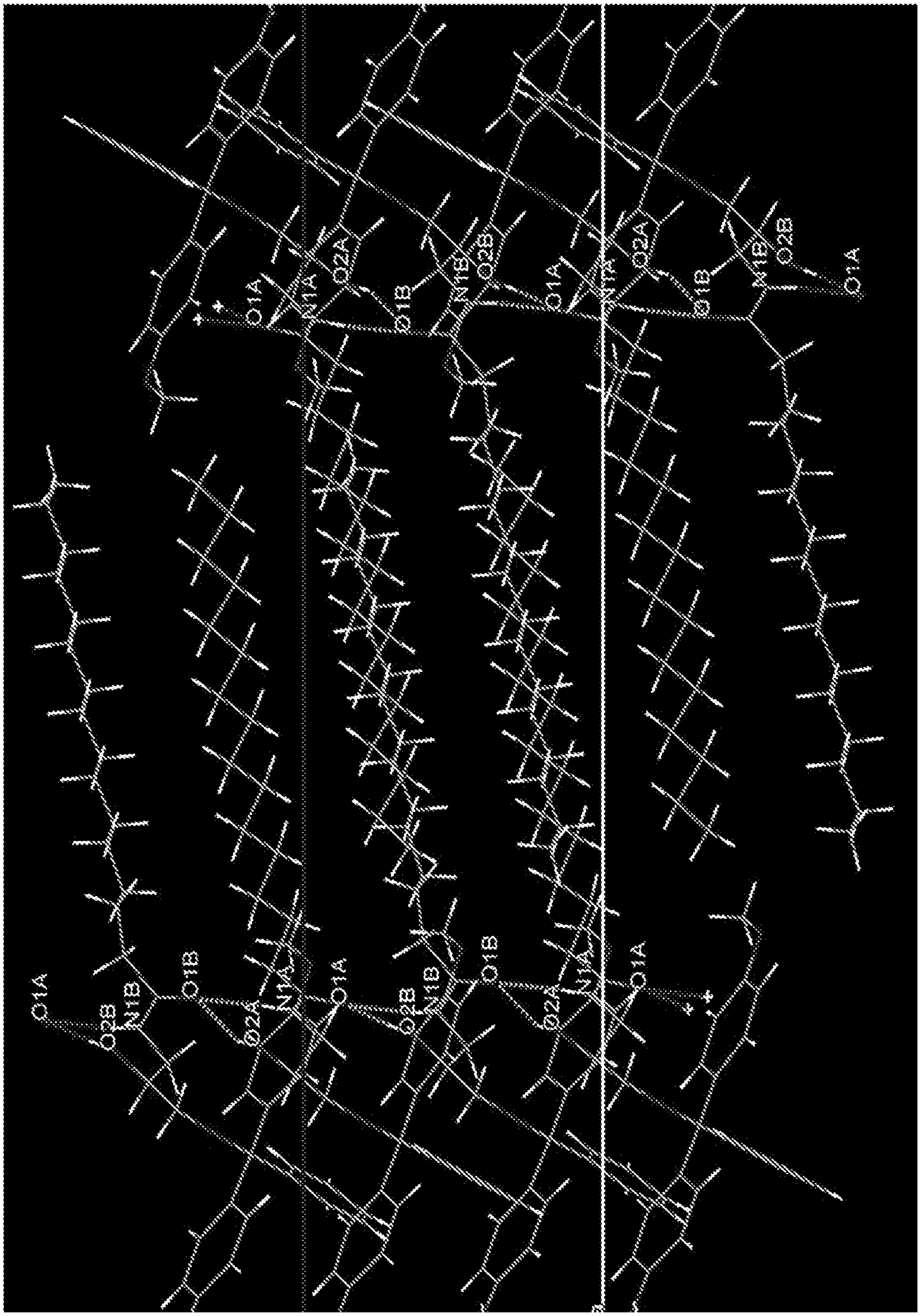

FIG. 4A depicts an Oak Ridge Thermal Ellipsoid Plot (ORTEP) diagram of the two different conformations of 3-palmitoyl-amido-2-hydroxy-1-dimethoxytriphenylmethylether-propane determined by X-ray crystallography. FIG. 4B depicts a unit cell of crystalline 3-palmitoyl-amido-2-hydroxy-1-dimethoxytriphenylmethylether-propane. FIG. 4C depicts a view of crystal packing of 3-palmitoyl-amido-2-hydroxy-1-dimethoxytriphenylmethylether-propane along a first axis. FIG. 4D depicts crystal packing of 3-palmitoyl-amido-2-hydroxy-1-dimethoxytriphenylmethylether-propane along a second axis. FIG. 4E depicts the intermolecular hydrogen bonding between conformer A and conformer B along the second crystallographic axis.

SELECT DEFINITIONS OF CHEMICAL TERMINOLOGY

The following terms have the following meanings unless otherwise indicated. Any undefined terms have their art recognized meanings.

As used herein, the terms "phosphate" and "phosphate group" are meant to encompass a thiophosphate group and an oxophosphate group.

As used herein, the term "phosphoramidite amino group" refers to the amino group, —$NR^4R^5$, attached to the phosphorus atom of a phosphoramidite group, and the term "phosphoramidite nitrogen" refers to the nitrogen atom of the phosphoramidite amino group.

"Alkyl" refers to monovalent saturated aliphatic hydrocarbyl groups having from 1 to 10 carbon atoms and such as 1 to 6 carbon atoms (e.g., "an alkyl of 1 to 6 carbons atoms"), or 1 to 5 (e.g., "an alkyl of 1 to 5 carbons atoms"), or 1 to 4 (e.g., "an alkyl of 1 to 4 carbons atoms"), or 1 to 3 carbon atoms (e.g., "an alkyl of 1 to 3 carbons atoms"). This term includes, by way of example, linear and branched hydrocarbyl groups such as methyl($CH_3$—), ethyl ($CH_3CH_2$—), n-propyl($CH_3CH_2CH_2$—), isopropyl (($CH_3)_2CH$—), n-butyl($CH_3CH_2CH_2CH_2$—), isobutyl (($CH_3)_2CHCH_2$—), sec-butyl(($CH_3$)($CH_3CH_2$)CH—), t-butyl(($CH_3)_3C$—), n-pentyl($CH_3CH_2CH_2CH_2CH_2$—), and neopentyl(($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —$S(O)_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —$NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic. In some instances, a"substituted alkyl" refers to an alkyl group as defined herein having from 1 to 5 substituents selected from the group consisting of alkoxy, cycloalkyl, cycloalkenyl, acyl, acylamino, acyloxy, amino, aminoacyl, aminoacyloxy, oxyaminoacyl, azido, cyano, halogen, hydroxyl, carboxyl, carboxylalkyl, thiol, thioalkoxy, aryl, aryloxy, heteroaryl, heteroaryloxy, heterocyclyl, heterocyclooxy, sulfonamido, and —$NR^aR^b$, wherein $R^a$ and $R^b$ may be the same or different and are chosen from hydrogen, alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —$NR^{10}$—, —$NR^{10}C$(O)—, —C(O)$NR^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—C$(CH_3)_2CH_2C(O)$—), (—$C(CH_3)_2CH_2C(O)NH$—), (—CH$(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups-alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups-alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group-alkylene-S-alkyl, alkylene-S-substituted alkyl, substituted alkylene- S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —$SO_2$-alkyl, —$SO_2$-substituted alkyl, —$SO_2$-aryl and —$SO_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —$SO_2$-alkyl, —$SO_2$-substituted alkyl, —$SO_2$-aryl, and —$SO_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3$C(O)—

"Acylamino" refers to the groups —$NR^{20}$C(O)alkyl, —$NR^{20}$C(O)substituted alkyl, N $R^{20}$C(O)cycloalkyl, —$NR^{20}$C(O)substituted cycloalkyl, —$NR^{20}$C(O)cycloalkenyl, —$NR^{20}$C(O)substituted cycloalkenyl, —$NR^{20}$C(O) alkenyl, —$NR^{20}$C(O)substituted alkenyl, —$NR^{20}$C(O)alkynyl, —$NR^{20}$C(O)substituted alkynyl, —$NR^{20}$C(O)aryl, —$NR^{20}$C(O)substituted aryl, —$NR^{20}$C(O)heteroaryl, —$NR^{20}$C(O)substituted heteroaryl, —$NR^{20}$C(O)heterocyclic, and —$NR^{20}$C(O)substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{21}$C(O)$NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl. In such cases, an aryl group that is substituted with from 1 to 5 substituents (e.g., as described herein) is referred to as a "substituted aryl".

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl. In such cases, a heteroaryl group that is substituted with from 1 to 5 substituents (e.g., as described herein) is referred to as a "substituted heteroaryl".

The term "heteroaralkyl" refers to the groups-alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —$NO_2$.

"Oxo" refers to the atom (=O).

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

"Sulfonyloxy" refers to the group —$OSO_2$-alkyl, $OSO_2$-substituted alkyl, $OSO_2$-alkenyl, $OSO_2$-substituted alkenyl, $OSO_2$-cycloalkyl, $OSO_2$-substituted cycloalkyl, $OSO_2$-cycloalkenyl, $OSO_2$-substituted cycloalkenyl, $OSO_2$-aryl, $OSO_2$-substituted aryl, $OSO_2$-heteroaryl, $OSO_2$-substituted heteroaryl, $OSO_2$-heterocyclic, and $OSO_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O$-$M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

"Stereoisomer" and "stereoisomers" refer to compounds that have same atomic connectivity but different atomic arrangement in space. Stereoisomers include cis-trans isomers, E and Z isomers, enantiomers, and diastereomers.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound. It is understood that the term "or a salt thereof" is intended to include all permutations of salts. It is understood that the term "or a pharmaceutically acceptable salt thereof" is intended to include all permutations of salts. It is understood that the term "or a solvate thereof" is intended to include all permutations of solvates. It is understood that the term "or a stereoisomer thereof" is intended to include all permutations of stereoisomers. It is understood that the term "or a tautomer thereof" is intended to include all permutations of tautomers. Thus for example it follows that it is intended to include a solvate of a pharmaceutically acceptable salt of a tautomer of a stereoisomer of subject compound.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, methods and materials of interest are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. When possible, this nomenclature has generally been derived using the commercially-available AutoNom software (MDL, San Leandro, Calif.).

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{1}C$, $^{13}C$, $^{14}C$, $^{15}N$, $^{18}O$ $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

DETAILED DESCRIPTION

Aspects of the disclosure include crystalline solids of 3-palmitoyl-amido-1,2-propanediol (Formula I):

(I)

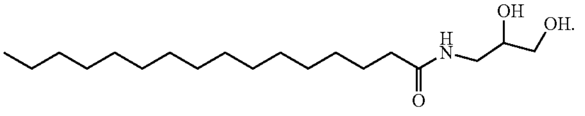

The term "crystalline" is used herein in its conventional sense to refer to a solid material where the molecules that form the solid are arranged in a highly ordered microscopic geometric configuration (e.g., form an ordered lattice-type structure) that extends in three dimensions. In embodiments, crystalline solids described herein are not amorphous, which are characterized by undefined structural order and microscopic configurations that lack a regular geometric arrangement in three dimensions.

In embodiments, the crystalline solid of 3-palmitoyl-amido-1,2-propanediol has a polymorph purity (i.e., is present as the polymorph as evidenced by X-ray powder diffraction (XRPD) analysis, thermogravimetric analysis (TGA) and differential scanning calorimetry (DSC) analysis, described in greater detail below) that is 90% or greater, such as 95% or greater, such as 97% or greater, such as 99% or greater and including 99.9% or greater. In some embodiments, the polymorph form of 3-palmitoyl-amido-1,2-propanediol described herein is present in the crystalline solid in 100% purity. In some embodiments, the polymorph form of the crystalline solid of 3-palmitoyl-amido-1,2-propanediol provided herein exhibits improved solubility and reactivity as compared to other polymorphs of crystalline 3-palmitoyl-amido-1,2-propanediol and amorphous 3-palmitoyl-amido-1,2-propanediol.

In embodiments, the polymorph form of crystalline solid 3-palmitoyl-amido-1,2-propanediol exhibits an X-ray powder diffraction (XRPD) pattern that includes a peak at about 8.25° 2Θ. For a given crystal form, the relative intensity of a diffraction peak may vary due to orientation of the crystal relative to the x-rays such as from crystalline morphology. In embodiments, the intensity of x-ray powder differaction peak in 20 may vary from crystal to crystal, but the characteristic peak positions for the polymorph form will remain the same. In certain embodiments, the polymorph form of the crystalline solid 3-palmitoyl-amido-1,2-propanediol has a x-ray powder diffraction (XRPD) pattern that includes one or more peaks at about 2.75° 2Θ; about 6° 2Θ; about 3.8° 2Θ; about 15° 2Θ; about 26.3° 2Θ; about 30.5° 2Θ and about 33.1° 2Θ. The polymorph form of the crystalline solid of 3-palmitoyl-amido-1,2-propanediol provided herein is, in some instances, characterized by a single weight loss step by thermogravimetric analysis (TGA). In certain instances, the weight loss step begins at about 200.5° C.

Differential scanning calorimetry (DSC) measures the transition temperature of a crystalline solid when the crystal absorbs or releases heat due to a change in its structure or due to melting. DSC provides for distinguishing between different crystalline forms (e.g., different polymorphs). Different crystal forms may be identified according to their different characteristic transition temperatures. In some embodiments, the polymorph form of crystalline solid of 3-palmitoyl-amido-1,2-propanediol provided herein exhibits a first endotherm at about 79.3° C. and a second endotherm at about 102.5° C. by differential scanning calorimetry (DSC). In these embodiments, the second endotherm is a single peak endotherm.

Methods for preparing the polymorph form of crystalline solid of 3-palmitoyl-amido-1,2-propanediol are also provided. In practicing methods according to certain embodiments, 3-palmitoyl-amido-1,2-propanediol is contacted with one or more solvents to produce a 3-palmitoyl-amido-1,2-propanediol composition and precipitated to produce a 3-palmitoyl-amido-1,2-propanediol crystalline solid. In some embodiments, the solvent is a polar solvent. In other embodiments, the solvent is a non-polar solvent. In still other embodiments, the solvent is mixture of a polar solvent and a non-polar solvent. Solvents of interest may include, but are not limited to, tetrahydrofuran, methyltetrahydrofuran, dichloromethane, isopropylacetate, ethyl acetate, 1,2-dichloroethane (DCE), dimethylformamide (DMF), acetone, dimethylacetamide, dimethylsulfoxide (DMSO), acetonitrile, toluene, 2-methylbutan-2-ol (tAmOH) and N-methyl-2-pyrrolidone (NMP) and combinations thereof. In some instances, the solvent is selected from tetrahydrofuran, methyl-tetrahydrofuran and dichloromethane. In certain instances, the solvent is tetrahydrofuran.

In certain embodiments, the 3-palmitoyl-amido-1,2-propanediol is contacted with the solvent in the presence of a base. In some instances, the base is an organic base. The organic base used may include, but is not limited to, triethylamine, triethanolamine, ammonia, arginine, benzathine, ethylenediamine, meglumine, procaine, N-methylglucamine, piperazine, tromethamine, N,N'-dibenzylethylenediamine, chloroprocaine, diethanolamine, ethanolamine, diisopropylamine, diisopropylethylamine, 1,8-bis(dimethylamino)naphthalene (proton sponge), imidazole, 1,8-diazabicyclo[5.4.0]undec-7-ene (DBU), 2,4,6-trimethylpyridine (collidine), potassium carbonate, sodium methoxide, tetramethylethylenediamine (TMEDA) and dimethylaminoethanol among other organic bases. In some instances, the base is selected from tetramethylethylenediamine (TMEDA), 1,8-bis(dimethylamino)naphthalene (proton sponge) and triethylamine. In certain instances, the base is triethylamine. The amount of base contacted with the 3-palmitoyl-amido-1,2-propanediol may vary, ranging from 1 equivalent to 4 equivalents of base to 3-palmitoyl-amido-1,2-propanediol, such as from 1.5 equivalents to 3.5 equivalents and including about 3 equivalents of base to 3-palmitoyl-amido-1,2-propanediol.

To precipitate the crystalline solid of 3-palmitoyl-amido-1,2-propanediol, the 3-palmitoyl-amido-1,2-propanediol solvent composition (with or without base) may be first heated to produce a heated 3-palmitoyl-amido-1,2-propanediol solvent composition and then cooled to form the crystalline solid 3-palmitoyl-amido-1,2-propanediol. The 3-palmitoyl-amido-1,2-propanediol solvent composition may be heated to a temperature that ranges from 10° C. to 60° C., such as from 15° C. to 55° C., such as from 25° C. to 55° C. and including to 50° C. The heated composition may be maintained at the elevated temperature for a duration that varies, such as for 1 minute or longer, such as for 2 minutes or longer, such as for 5 minutes or longer, such as 10 minutes or longer, such as 15 minutes or longer, such as 30 minutes or longer and including for 60 minutes or longer. In certain embodiments, the 3-palmitoyl-amido-1,2-propanediol solvent is heated to a temperature sufficient to solubilize the 3-palmitoyl-amido-1,2-propanediol in the solvent. All or part of the amount of 3-palmitoyl-amido-1,2-propanediol may be solubilized in the solvent (e.g., the 3-palmitoyl-amido-1,2-propanediol solvent composition may range, when inspected with the naked eye, from a clear solution to a slurry composition), such as 25% or more by weight of the 3-palmitoyl-amido-1,2-propanediol may be solubilized into the solvent, such as 50% or more, such as 75% or more, such as 90% or more, such as 95% or more, such as 97% or more and including 99% or more.

In embodiments, the crystalline solid of 3-palmitoyl-amido-1,2-propanediol is precipitated by cooling the heated 3-palmitoyl-amido-1,2-propanediol solvent composition. The composition may be cooled to a temperature of 20° C. to 40° C., such as from 15° C. to 35° C. and including about 30° C. In certain embodiments, methods include precipitating the crystalline solid of 3-palmitoyl-amido-1,2-propanediol by removing an amount of the solvent from the composition, such as by roto-evaporation or under inert gas ($N_2$ or argon).

In certain embodiments, the crystalline solid of 3-palmitoyl-amido-1,2-propanediol is isolated by filtration (e.g., vacuum filtration) or the solvent may be removed by heating or roto-evaporation. In certain embodiments, the crystalline solid of 3-palmitoyl-amido-1,2-propanediol is isolated by drying at room temperature under nitrogen atmosphere or under vacuum.

Aspects of the disclosure also include a crystalline solid of 3-palmitoyl-amido-2-hydroxy-1-dimethoxytriphenylmethylether-propane (Formula III):

(III)

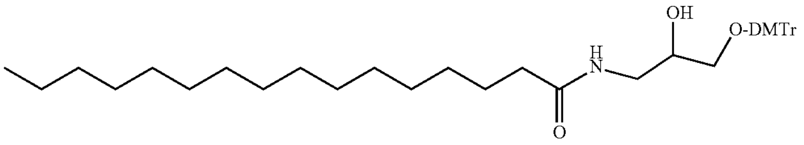

where DMTr is dimethoxytriphenylmethyl. In certain instances, the crystalline solid of 3-palmitoyl-amido-2-hydroxy-1-dimethoxytriphenylmethylether-propane is a single crystal of 3-palmitoyl-amido-2-hydroxy-1-dimethoxytriphenylmethylether-propane. The term "single crystal" is used herein in its conventional sense to refer to a monocrystalline solid in which the crystal lattice of the entire sample is continuous and unbroken to the edges of the sample, with no grain boundaries. In certain embodiments, single crystals of interest are monocrystalline solids of 3-palmitoyl-amido-2-hydroxy-1-dimethoxytriphenylmethylether-propane of a size and quality sufficient for X-ray crystallography (XRC) and X-ray crystal structure determination.

In embodiments, the crystalline solid of 3-palmitoyl-amido-2-hydroxy-1-dimethoxytriphenylmethylether-propane has a purity (e.g., single crystals of 3-palmitoyl-amido-2-hydroxy-1-dimethoxytriphenylmethylether-propane) that is 90% or greater, such as 95% or greater, such as 97% or greater, such as 99% or greater and including 99.9% or greater. In some embodiments, 3-palmitoyl-amido-2-hydroxy-1-dimethoxytriphenylmethylether-propane is present in the crystalline solid in 100% purity. In some embodiments, the crystalline solid of 3-palmitoyl-amido-2-hydroxy-1-dimethoxytriphenylmethylether-propane (e.g., single crystals of 3-palmitoyl-amido-2-hydroxy-1-dimethoxytriphenylmethylether-propane) provided herein exhibits improved solubility and reactivity as compared to other crystalline forms (e.g., powdered) or amorphous solid 3-palmitoyl-amido-2-hydroxy-1-dimethoxytriphenylmethylether-propane.

The crystalline solid of 3-palmitoyl-amido-2-hydroxy-1-dimethoxytriphenylmethylether-propane, according to embodiments, is in monoclinic crystalline form. Each unit cell in the crystalline solid includes two different conformations of 3-palmitoyl-amido-2-hydroxy-1-dimethoxytriphenylmethylether-propane, such as a bent conformation and a linear conformation. In embodiments, each conformation (bent and linear) of 3-palmitoyl-amido-2-hydroxy-1-dimethoxytriphenylmethylether-propane is present in the unit cell in a ratio of 1:1. Each unit cell in the crystalline solid includes 4 molecules of 3-palmitoyl-amido-2-hydroxy-1-dimethoxytriphenylmethylether-propane. In some embodiments, the unit cell has dimensions of about 8.44 Å×about 26.56 Å×about 10.06 Å, where the volume of the unit cell is about 2254.8 $Å^3$. The subject 3-palmitoyl-amido-2-hydroxy-1-dimethoxytriphenylmethylether-propane crystalline solids have a density of from about 1.2 $g/cm^3$ to about 1.3 $g/cm^3$ and have a purity of 95% or more.

Methods for preparing the crystalline solid (e.g., single crystals) of 3-palmitoyl-amido-2-hydroxy-1-dimethoxytriphenylmethylether-propane are also provided. In practicing methods according to certain embodiments, 3-palmitoyl-amido-2-hydroxy-1-dimethoxytriphenylmethylether-propane is contacted with one or more solvents to produce a 3-palmitoyl-amido-2-hydroxy-1-dimethoxytriphenylmethylether-propane composition and precipitated to produce a 3-palmitoyl-amido-2-hydroxy-1-dimethoxytriphenylmethylether-propane crystalline solid, such as one or more single crystals of 3-palmitoyl-amido-2-hydroxy-1-dimethoxytriphenylmethylether-propane.

In some embodiments, the solvent is a polar solvent. In other embodiments, the solvent is a non-polar solvent. In still other embodiments, the solvent is mixture of a polar solvent and a non-polar solvent. Solvents of interest may include, but are not limited to, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide, 2-methylbutan-2-ol (tAmOH), dimethyl sulfoxide, pentane, hexanes, heptane, octanane, among other solvents. In certain embodiments, the solvent is a mixture of dichloromethane and pentane.

To precipitate the 3-palmitoyl-amido-2-hydroxy-1-dimethoxytriphenylmethylether-propane crystalline solid, the 3-palmitoyl-amido-2-hydroxy-1-dimethoxytriphenylmethylether-propane solvent composition may be first heated to produce a heated 3-palmitoyl-amido-2-hydroxy-1-dimethoxytriphenylmethylether-propane solvent composition and then cooled to form the crystalline solid 3-palmitoyl-amido-2-hydroxy-1-dimethoxytriphenylmethylether-propane. The 3-palmitoyl-amido-2-hydroxy-1-dimethoxytriphenylmethylether-propane solvent composition may be heated to a temperature that ranges from 10° C. to 60° C., such as from 15° C. to 55° C., such as from 25° C. to 55° C. and including to 50° C. The heated composition may be maintained at the elevated temperature for a duration that varies, such as for 1 minute or longer, such as for 2 minutes or longer, such as for 5 minutes or longer, such as 10 minutes or longer, such as 15 minutes or longer, such as 30 minutes or longer and including for 60 minutes or longer. In certain embodiments, the 3-palmitoyl-amido-2-hydroxy-1-dimethoxytriphenylmethylether-propane solvent is heated to a temperature sufficient to solubilize the 3-palmitoyl-amido-2-hydroxy-1-dimethoxytriphenylmethylether-propane in the solvent.

In other embodiments, the crystalline solid of 3-palmitoyl-amido-2-hydroxy-1-dimethoxytriphenylmethylether-propane is precipitated by cooling the heated 3-palmitoyl-amido-2-hydroxy-1-dimethoxytriphenylmethylether-propane solvent composition. The composition may be cooled to a temperature of −20° C. to 20° C., such as from −19° C. to 19° C., such as from −18° C. to 18° C., such as from −17° C. to 17° C., such as from −16° C. to 16° C., such as from −15° C. to 15° C., such as from −14° C. to 14° C., such as from −13° C. to 13° C. such as from −12° C. to 12° C. such as from −11° C. to 11° C. and including from −10° C. to 10° C. In certain embodiments, methods include precipitating the crystalline solid of 3-palmitoyl-amido-2-hydroxy-1-dimethoxytriphenylmethylether-propane by removing the solvent from the composition, such as by roto-evaporation or under inert gas ($N_2$ or argon).

The crystalline solid of 3-palmitoyl-amido-2-hydroxy-1-dimethoxytriphenylmethylether-propane may be isolated by filtration (e.g., vacuum filtration) or the solvent may be removed by heating or roto-evaporation. In certain embodiments, the crystalline solid of 3-palmitoyl-amido-2-hydroxy-1-dimethoxytriphenylmethylether-propane is isolated by drying at room temperature under nitrogen atmosphere or under vacuum.

Methods for preparing 3-palmitoyl-amido-2-hydroxy-1-dimethoxytriphenylmethylether-propane from 3-palmitoyl-amido-1,2-propanediol are also described. In practicing the subject methods according to certain embodiments, a solvent is contacted with a crystalline solid of 3-palmitoyl-amido-1,2-propanediol to generate a precursor composition; and the precursor composition is contacted with a composition comprising dimethoxytriphenylmethyl chloride to generate a composition having 3-palmitoyl-amido-2-hydroxy-1-dimethoxytriphenylmethylether-propane.

In embodiments, solvents of interest may include, but are not limited to, tetrahydrofuran, methyltetrahydrofuran, dichloromethane, isopropylacetate (iPrOAc), ethyl acetate, 1,2-dichloroethane (DCE), dimethylformamide (DMF), acetone, dimethylsulfoxide (DMSO), acetonitrile, toluene, 2-methylbutan-2-ol (tAmOH), N-methyl-2-pyrrolidone (NMP) or a combination thereof. In some instances, the solvent is selected from tetrahydrofuran, methyltetrahydrofuran, dichloromethane, isopropylacetate, acetonitrile, toluene, 2-methylbutan-2-ol (tAmOH) and N-methyl-2-pyrrolidone (NMP). In certain instances, the solvent is selected from methyltetrahydrofuran, tetrahydrofuran and dichloromethane.

In some embodiments, the precursor composition includes an additive. For example, the additive may be calcium oxide, magnesium oxide, boric acid, tetra-n-butyl ammonium fluoride (TBAF), 4-dimethylaminopyridine (DMAP), copper chloride ($CuCl_2$), ytterbium (III) chloride ($YbCl_3$) or 1,4-diazabicyclo[2.2.2]octane (DABCO). In some instances, the additive is selected from tetra-n-butyl ammonium fluoride (TBAF), magnesium oxide and boric acid. In certain instances, the additive is magnesium oxide. The amount of additive in the precursor composition may vary, ranging from 0.05 equivalents to 1 equivalent of additive to 3-palmitoyl-amido-1,2-propanediol, such as from 0.1 equivalents to 0.5 equivalents and including about 0.3 equivalents of additive to 3-palmitoyl-amido-1,2-propanediol.

In some embodiments, the precursor composition is further contacted with a base. In certain instances, the base is an organic base. In some embodiments, the precursor composition is contacted with the protecting group in the presence of a base selected from 1,8-bis(dimethylamino)naphthalene (proton sponge), imidazole, 1,8-diazabicyclo[5.4.0]undec-7-ene (DBU), 2,4,6-trimethylpyridine (collidine), triethylamine (TEA), potassium carbonate, sodium methoxide, tetramethylethylenediamine (TMEDA), dimethylaminoethanol and combinations thereof. In some instances, the base is selected from 1,8-bis(dimethylamino)naphthalene (proton sponge), tetramethylethylenediamine (TMEDA) and triethylamine (TEA). In certain instances, the base is triethylamine.

The amount of base contacted with the 3-palmitoyl-amido-1,2-propanediol precursor composition may vary, ranging from 0.5 equivalents to 3.5 equivalents of base to 3-palmitoyl-amido-1,2-propanediol, such as from 0.75 equivalents to 1.95 equivalents, such as 1 equivalent to 1.9 equivalents, such as from 1.1 equivalents to 1.85 equivalents, such as from 1.15 equivalents to 1.80 equivalents, such as from 1.25 equivalents to 1.75 equivalents and including contacting 3-palmitoyl-amido-1,2-propanediol with 1.5 equivalents of base.

In some embodiments, the precursor composition is formed and maintained at ambient temperature. In other embodiments, the precursor composition is formed and maintained at an elevated temperature, such as from 25° C. to 40° C., such as from 27.5° C. to 45° C. and including from 30° C. to 35° C., such as at about 30° C. In certain embodiments, the precursor composition is formed at a first temperature and changed to a second temperature. In one example, the precursor composition is formed at ambient temperature and then changed to an elevated temperature, e.g., from 25° C. to 40° C., such as from 27.5° C. to 45° C. and including from 30° C. to 35° C., such as at about 30° C. In another example, the precursor composition is formed at an elevated temperature e.g., (about 50° C. or more) and is cooled to a lower temperature (e.g., about 30° C.) before contacting the precursor composition with the protecting group.

In embodiments, the precursor composition is contacted with a hydroxyl protecting group to generate a 3-palmitoyl-amido)-2-hydroxy-1-(protected hydroxy)-propane. The hydroxyl protecting group may vary, where in certain instances, the hydroxyl protective group includes, but is not limited to: 1) an alkyl ether-type protective group, such as an alkyl ether, allyl ether, triphenylmethyl ether, dimethoxytriphenylmethyl ether, benzyl ether or p-methoxybenzyl ether protecting group; 2) an ester and carbonate-type protective group, such as an acetate, chloroacetate, dichloroacetate, trichloroacetate, trifluoroacetate, pivaloate, benzoate, p-methoxybenzoate, p-bromobenzoate, methyl carbonate, 9-(fluorenylmethyl) carbonate (Fmoc), allyl carbonate (Alloc), 2,2,2-trichloroethyl carbonate (Troc), 2-(trimethylsilyl)ethyl carbonate (Teoc), benzyl carbonate (Cbz), t-butyl carbonate (Boc) or dimethylthiocarbmate (DMTC) protecting group; 3) an acetal type protective group, such as a methoxymethyl ether (MOM), benzyloxymethyl ether (BOM), 2,2,2-trichloroethoxymethyl ether, 2-methoxymethyl ether (MEM), methylthiomethyl ether (MTM), p-methoxybenzyloxymethyl ether (PMBM), 2-(trimethylsilyl)ethoxymethyl ether (SEM), tetrahydropyranyl ether (THP) protecting group; and 2) a silyl ether type protective group, such as a trimethylsilyl (TMS), triethylsilyl (TES), isopropyldimethylsilyl (IPDMS), diethylisopropylsilyl (DEIPS), t-butyldimethylsilyl (TBS), t-butyldiphenylsilyl (TBDPS), triisopropylsilyl (TIPS), tetraisopropyldisiloxanylidene (TIPDS) or di-t-butylsilylene (DTBS) protecting group. In certain embodiments, the hydroxyl protecting group is a dimethoxy-triphenylmethyl protecting group.

The amount of hydroxyl protecting group contacted with the precursor composition may vary, ranging from 0.5 equivalents to 2 equivalent of additive to 3-palmitoyl-amido-1,2-propanediol, such as from 0.75 equivalents to 1.5 equivalents and including about 1.4 equivalents of hydroxyl protecting group to 3-palmitoyl-amido-1,2-propanediol.

In some embodiments, 3-palmitoyl-amido-1,2-propanediol used in the method for preparing 3-palmitoyl-amido-2-hydroxy-1-dimethoxytriphenylmethylether-propane is a crystalline solid of 3-palmitoyl-amido-1,2-propanediol. In certain embodiments, 3-palmitoyl-amido-1,2-propanediol is a polymorph form of crystalline solid 3-palmitoyl-amido-1,2-propanediol that exhibits an X-ray powder diffraction (XRPD) pattern having one or more peaks at about 2.75° 2Θ; about 6° 2Θ; about 3.8° 2Θ; about 8.25° 2Θ about 15° 2Θ; about 26.3° 2Θ; about 30.5° 2Θ and about 33.1° 2Θ.

The components used in each step of the subject methods may be a purified composition or a crude composition as desired. The term "purified" is used in its conventional sense to refer to a composition where at least some isolation or purification process has been conducted, such as for example, filtration or aqueous workup of a reaction mixture. In certain instances, purification includes liquid chromatography, recrystallization, distillation (e.g., azeotropic distillation) or other type of compound purification. In some embodiments, a reaction mixture is used in a subsequent step in the methods described herein as a crude mixture where no purification or other workup of the reaction mixture has been conducted. In certain instances, the crude composition reaction mixtures include the compound of interest in sufficient purity such as where the crude composition includes a compound of interest in a purity of 90% or greater, such as 95% or greater, such as 97% or greater and including 99% or greater, as determined by high performance liquid chromatography (HPLC), proton nuclear magnetic resonance spectroscopy ($^1$H NMR) or a combination thereof.

Aspects of the Disclosure

Aspects, including embodiments, of the subject matter described herein may be beneficial alone or in combination, with one or more other aspects or embodiments. Without limiting the description, certain non-limiting aspects of the disclosure numbered 1-66 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A crystalline solid of a compound of Formula I:

(I)

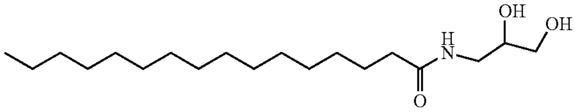

2. The crystalline solid of 1, having an x-ray powder diffraction (XRPD) pattern comprising a peak at about 8.25° 2Θ.
3. The crystalline solid of claim any one of 1-2, having an XRPD pattern comprising one or more peaks at about 2.75° 2Θ; about 6° 2Θ; about 3.8° 2Θ; about 15° 2Θ; about 26.3° 2Θ; about 30.5° 2Θ and about 33.1° 2Θ.
4. The crystalline solid of any one of 1-3, wherein thermogravimetric analysis (TGA) of the crystalline solid is characterized by a single weight loss step.
5. The crystalline solid of 4, wherein the weight loss step begins at about 200.5° C.
6. The crystalline solid of any one of 1-5, having a first endotherm at 79.3° C. and a second endotherm at about 102.5° C. by differential scanning calorimetry (DSC).
7. The crystalline solid of 6, wherein the second endotherm is a single peak endotherm.
8. A method comprising:
contacting a solvent with a compound of Formula I:

(I)

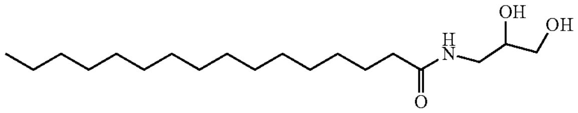

to generate a precursor composition; and
generating a crystalline solid of the compound of Formula I from the precursor composition.
9. The method of 8, wherein the solvent is selected from the group consisting of tetrahydrofuran, methyltetrahydrofuran, dichloromethane, isopropylacetate, ethyl acetate, 1,2-dichloroethane (DCE), dimethylformamide (DMF), acetone, dimethylacetamide, dimethylsulfoxide (DMSO), acetonitrile, toluene, 2-methylbutan-2-ol (tAmOH) and N-methyl-2-pyrrolidone (NMP) and a combination thereof.
10. The method of 9, wherein the solvent is selected from tetrahydrofuran, methyltetrahydrofuran and dichloromethane.
11. The method of 10, wherein the solvent is tetrahydrofuran.
12. The method of any one of 8-11, wherein generating the crystalline solid of the compound of Formula I comprises:
heating the precursor composition to a temperature of from about 45° C. to about 65° C.; and
cooling the heated precursor composition to a temperature of from about 25° C. to about 35° C. to generate the crystalline solid of the compound of Formula I.
13. The method of 12, wherein generating the crystalline solid of the compound of Formula I comprises heating the precursor composition to a temperature of about 50° C. and cooling the heated precursor composition to a temperature of about 30° C. to generate the crystalline solid of Formula I.
14. The method of any one of 8-13, wherein the compound of Formula I is contacted with the solvent in the presence of a base.
15. The method of 14, wherein the base is triethylamine (TEA).
16. The method of any one of 8-15, wherein the crystalline solid of the compound of Formula I has an x-ray powder diffraction (XRPD) pattern comprising a peak at about 8.25° 2Θ.

17. The method of any one of 8-16, wherein the crystalline solid of the compound of Formula I has an XRPD pattern comprising one or more peaks at about 2.75° 2Θ; about 6° 2Θ; about 3.8° 2Θ; about 15° 2Θ; about 26.3° 2Θ; about 30.5° 2Θ and about 33.1° 2Θ.
18. The method of any one of 8-17, wherein the crystalline solid of the compound of Formula I is characterized by a single weight loss step by thermogravimetric analysis (TGA).
19. The method of 18, wherein the weight loss step begins at about 200.48° C.
20. The method of any one of 8-19, wherein the crystalline solid of the compound of Formula I exhibits a first endotherm at 79.3° C. and a second endotherm at about 102.5° C. by differential scanning calorimetry (DSC).
21. The method of 20, wherein the second endotherm is a single peak endotherm.
22. A method comprising:
contacting a solvent with a crystalline solid of a compound of Formula I:

(I)

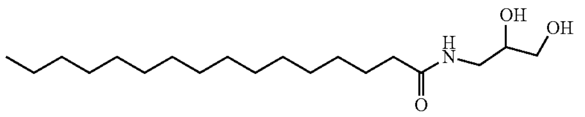

to generate a precursor composition; and
contacting the precursor composition with a composition comprising dimethoxytriphenylmethyl chloride to generate a composition comprising a compound of Formula II:

28. The method of any one of 22-27, wherein the precursor composition is contacted with dimethoxytriphenylmethyl chloride in the presence of an additive.
29. The method of 28, wherein the additive is selected from the group consisting of calcium oxide, magnesium oxide, boric acid, tetra-n-butyl ammonium fluoride (TBAF), 4-dimethylaminopyridine (DMAP), copper chloride ($CuCl_2$), ytterbium (III) chloride ($YbCl_3$) and 1,4-diazabicyclo[2.2.2]octane (DABCO).
30. The method of 29, wherein the additive is selected from tetra-n-butyl ammonium fluoride (TBAF), magnesium oxide and boric acid.
31. The method of 29, wherein the additive is magnesium oxide.
32. The method of any one of 22-31, wherein the solvent is selected from the group consisting of tetrahydrofuran, methyltetrahydrofuran, dichloromethane, isopropylacetate, ethyl acetate, 1,2-dichloroethane (DCE), dimethylformamide (DMF), acetone, dimethylsulfoxide (DMSO), acetonitrile, toluene, 2-methylbutan-2-ol (tAmOH) and N-methyl-2-pyrrolidone (NMP) and a combination thereof.
33. The method of 32, wherein the solvent is selected from tetrahydrofuran, methyltetrahydrofuran, dichloromethane, isopropylacetate, acetonitrile, toluene, 2-methylbutan-2-ol (tAmOH) and N-methyl-2-pyrrolidone (NMP).
34. The method of 32, wherein the solvent is selected from methyltetrahydrofuran, tetrahydrofuran and dichloromethane.
35. The method of any one of 22-34, wherein the crystalline solid of the compound of Formula I has an x-ray powder diffraction (XRPD) pattern comprising a peak at about 8.25° 2Θ.

(II)

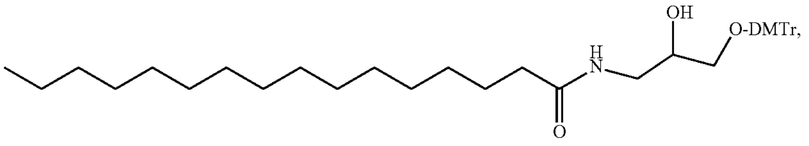

wherein DMTr is dimethoxytriphenylmethyl.
23. The method of 22, wherein the precursor composition is contacted with dimethoxytriphenylmethyl chloridein the presence of a base.
24. The method of 23, wherein the base in an organic base.
25. The method of 23, wherein the base is selected from the group consisting of 1,8-bis(dimethylamino)naphthalene (proton sponge), imidazole, 1,8-diazabicyclo [5.4.0]undec-7-ene (DBU), 2,4,6-trimethylpyridine (collidine), triethylamine (TEA), potassium carbonate, sodium methoxide, tetramethylethylenediamine (TMEDA) and dimethylaminoethanol.
26. The method of 23, wherein the base is selected from 1,8-bis(dimethylamino)naphthalene (proton sponge), tetramethylethylenediamine (TMEDA) and triethylamine (TEA).
27. The method of 23, wherein the base is triethylamine (TEA).
36. The method of any one of 22-35, wherein the crystalline solid of the compound of Formula I has an XRPD pattern comprising one or more peaks at about 2.75° 2Θ; about 6° 2Θ; about 3.8° 2Θ; about 15° 2Θ; about 26.3° 2Θ; about 30.5° 2Θ and about 33.1° 2Θ.
37. The method of any one of 22-36, wherein the crystalline solid of the compound of Formula I is characterized by a single weight loss step by thermogravimetric analysis (TGA).
38. The method of 37, wherein the weight loss step begins at about 200.48° C.
39. The method of any one of 22-38, wherein the crystalline solid of the compound of Formula I exhibits a first endotherm at 79.3° C. and a second endotherm at about 102.5° C. by differential scanning calorimetry (DSC).
40. The method of 39, wherein the second endotherm is a single peak endotherm.

41. A crystalline solid of a compound of Formula II:

(II)

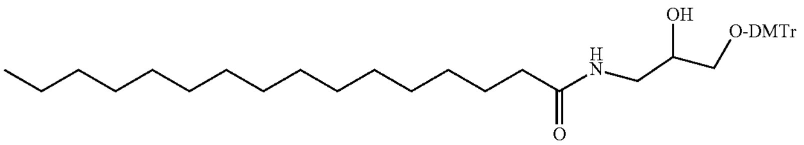

wherein DMTr is dimethoxytriphenylmethyl.

42. The crystalline solid of 41, wherein the crystalline solid of Formula II is in monoclinic crystalline form.

43. The crystalline solid of any one of 40-42, wherein each unit cell in the crystalline solid comprises two different conformations of the compound of Formula II.

44. The crystalline solid of 43, wherein each unit cell comprises an extended conformation and a bent conformation of the compound of Formula II.

45. The crystalline solid of any one of 43-44, wherein each conformation of the compound of Formula II is present in a ratio of 1:1.

46. The crystalline solid of any one of 41-45, wherein each unit cell of the crystalline solid comprises 4 molecules of the compound of Formula II.

47. The crystalline solid of 46, wherein the unit cell has dimensions of about 8.44 Å×about 26.56 Å×about 10.06 Å.

48. The crystalline solid of 47, wherein the unit cell has a volume of about 2254.8 $Å^3$.

49. The crystalline solid of 48, having a density of from about 1.2 $g/cm^3$ to about 1.3 $g/cm^3$.

50. The crystalline solid of any one of 41-49, wherein the compound of Formula II has a polymorph purity of 95% or more.

51. A method comprising:

contacting a composition comprising one or more solvents with a compound of Formula III:

58. The method of any one of 51-57, wherein one or more of the formed single crystals is in monoclinic crystalline form.

59. The method of any one of 51-58, wherein each single crystal comprises two different conformations of the compound of Formula II.

60. The method of 59, wherein each unit cell of the single crystal comprises an extended conformation and a bent conformation of the compound of Formula II.

61. The method of any one of 59-60, wherein each conformation of the compound of Formula II is present in each unit cell in a ratio of 1:1.

62. The method of any one of 51-61, wherein the unit cell of each single crystal comprises 4 molecules of the compound of Formula II.

63. The method of 62, wherein the unit cell has dimensions of about 8.44 Å×about 26.56 Å×about 10.06 Å.

64. The method of 63, wherein the unit cell has a volume of about 2254.8 Å.

65. The method of any one of 51-64, wherein each formed single crystal has a density of from about 1.2 $g/cm^3$ to about 1.3 $g/cm^3$.

66. The method of any one of 51-65, wherein each formed single crystal has polymorph purity of the compound of Formula II of 95% or more.

(II)

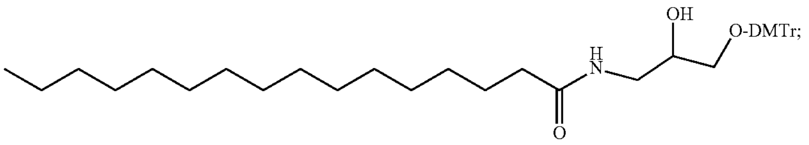

forming one or more single crystals of the compound of Formula II.

52. The method of 51, wherein the composition comprises two different solvents.

53. The method of 52, wherein the composition comprises a polar solvent and a non-polar solvent.

54. The method of 53, wherein the polar solvent is dichloromethane.

55. The method of any of 53-54, wherein the non-polar solvent is pentane.

56. The method of any one of 51-55, wherein the composition is contacted with the compound of Formula II at a temperature of from 10° C. to about 75° C.

57. The method of 56, wherein the method comprises heating the composition sufficient to dissolve the compound of Formula II and cooling the heated composition after the compound of Formula II is dissolved.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or see, second(s); min, minute(s); h or hr, hour(s); aa, amino acid(s);

kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described below.

Example 1-Preparation and Analysis of Crystalline Polymorphs of 3-Palmitoyl-Amido-1,2-Propanediol A screening of the solubility of 3-palmitoyl-amido-1,2-propanediol was conducted with various solvents and solvent mixtures. Tetrahydrofuran (THF), 2-methyl-THF, dichloromethane (DCM), N-methyl-2-pyrrolidone (NMP), dimethylacetamide (DMAc), toluene, 2-methylbutan-2-ol (tAmOH), isopropylacetate (iPrOAc), dimethylsulfoxide (DMSO) and dimethylformaide (DMF) were identified as solvents for use in the studies. The effect of triethylamine on the solubility was also evaluated. Triethylamine was shown to have a small effect on the solubility of 3-palmitoyl-amido-1,2-propanediol in these solvents. Dimethylacetamide (DMAc), dimethylsulfoxide (DMSO) and dimethylformaide (DMF) were determined to have moderate solubility of 3-palmitoyl-amido-1,2-propanediol.

Crystalline solids were identified as a new polymorph of 3-palmitoyl-amido-1,2-propanediol using THF, 2-methyl-THF or DCM with triethylamine during a heat/cool induced crystallization. The heat/cool crystallization included solubilizing 3-palmitoyl-amido-1,2-propanediol in a solution of THF, and heating and maintaining the composition at 50° C. overnight. For 2-methyl-THF or DCM, the solution with palmitoyl-amido-1,2-propanediol was heated to 60° C. overnight to produce a solution. After cooling the samples back to 30° C., crystalline solids formed as slurries in the solutions of THF, 2-methyl-THF and DCM.

The polymorphs of 3-palmitoyl-amido-1,2-propanediol formed exhibited faster solubility and showed greater reaction selectivity when used as a substrate in the preparation of 3-palmitoyl-amido-2-hydroxy-1-dimethoxytriphenylmethylether-propane.

Figure 1:
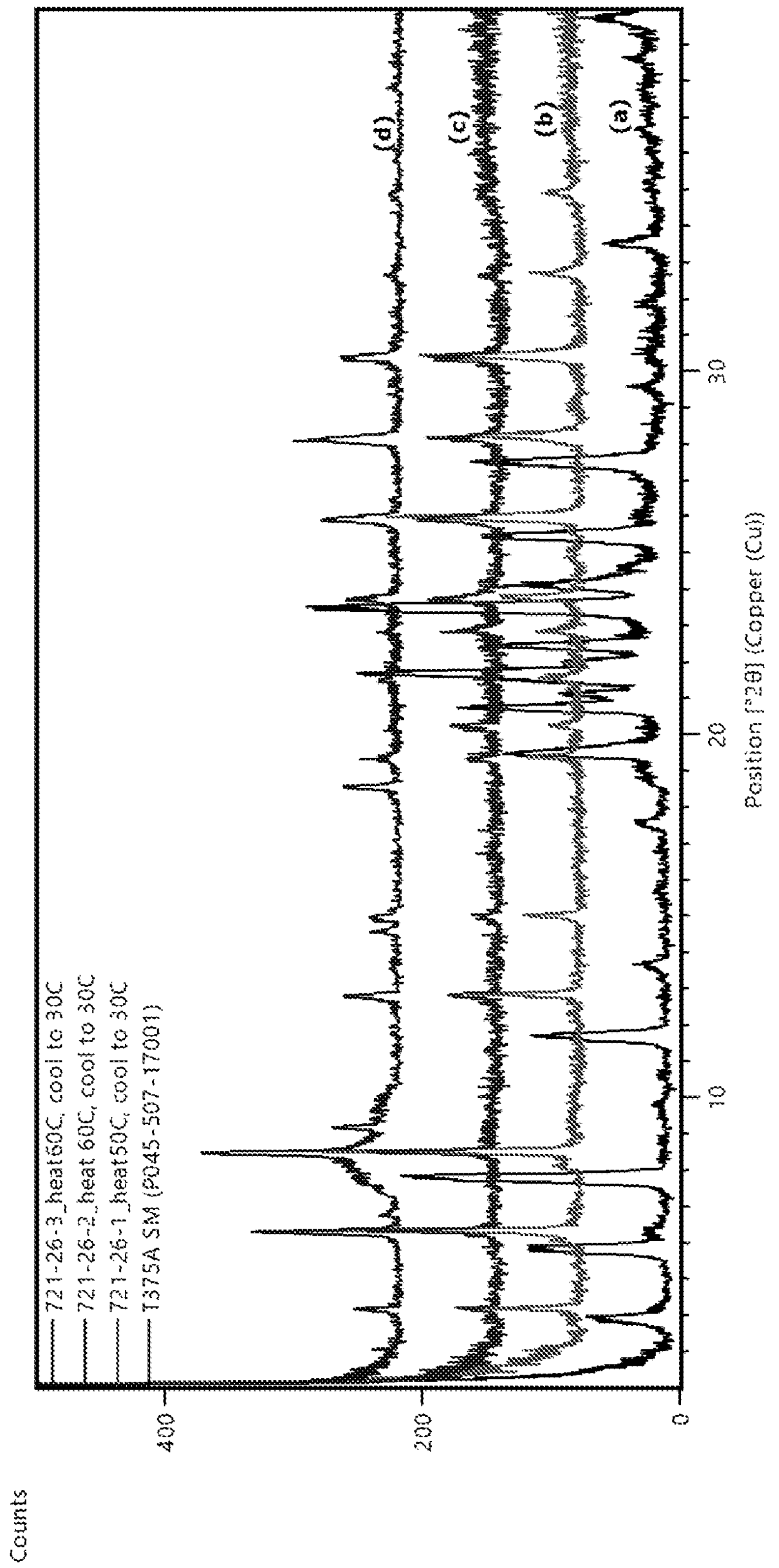
FIG. 1 shows the X-ray powder diffraction patterns of a polymorphic crystalline solid of 3-palmitoyl-amido-1,2-pro-

Analysis of the crystalline solids was conducted by X-ray powder diffraction (as a drop of slurry), thermogravimetric analysis, differential scanning calorimetry and nuclear magnetic resonance spectroscopy. FIG. 1 depicts the X-ray powder diffraction pattern (XRPD) of crystalline solids formed from the solutions of (b) THF, (c) 2-methyl THF and (d) DCM and a comparison of the peaks with the (a) 3-palmitoyl-amido-1,2-propanediol starting material. As shown in FIG. 1, the crystalline solids formed from THF, 2-methyl THF and DCM exhibit different peaks from the 3-palmitoyl-amido-1,2-propanediol starting material (e.g., at about 2.75° 2Θ; about 6° 2Θ; about 3.8° 2Θ; about 8.25 2Θ; about 15° 2Θ; about 26.3° 2Θ; about 30.5° 2Θ and about 33.1° 2Θ).

FIG. 2 depicts thermogravimetric analysis of crystalline solids formed from solutions of THF. The TGA of the polymorph of 3-palmitoyl-amido-1,2-propanediol formed from THF was characterized by a single weight loss step, which begins at about 200.5° C. The graph in FIG. 2 also depicts differential scanning calorimetry of crystalline solids formed from solutions of THF. FIG. 2 depicts the DSC plot of the polymorph of 3-palmitoyl-amido-1,2-propanediol formed from THF, which exhibited two endotherms, a first at about 79.9° C. and a second endotherm at about 102.5° C. The second endotherm peak at about 102.5° C. was a single peak endotherm. FIG. 3 depicts a comparison of the DSC plot of the polymorph of 3-palmitoyl-amido-1,2-propanediol formed from THF and that of the 3-palmitoyl-amido-1,2-propanediol starting material. The 3-palmitoyl-amido-1,2-propanediol starting material exhibits a first endotherm at about about 79.3° C. and a second endotherm at about 105.8° C.

Example 2-Preparation of 3-palmitoyl-amido-2-hydroxy-1-dimethoxytriphenylmethylether-propane (Compound B) from 3-palmitoyl-amido-1,2-propanediol (Compound A)

The reaction of 3-palmitoyl-amido-1,2-propanediol (CMPD-A) with 4,4'-dimethoxytriphenylmethyl chloride was tested in different bases and solvents. Different additives to the reaction mixture were also tested. Table 1 summarizes the reaction products formed: 3-palmitoyl-amido-2-hydroxy-1-dimethoxytriphenylmethylether-propane (CMPD-B), 3-palmitoyl-amido-1-hydroxy-2-dimethoxytriphenylmethylether-propane (CMPD-B-Reg), 3-palmitoyl-amido-1,2-dimethoxytriphenylmethylether-propane (Bis-DMTr). For each reaction, 3-palmitoyl-amido-1,2-propanediol was charged into a three-neck round bottom flask with the solvent at 30° C. and stirred for 1 hour. To the 3-palmitoyl-amido-1,2-propanediol solvent composition, 3.0 equivalents of base was added and stirred at 30° C. Where additive was used, 0.3 equivalents of additive was contacted with the reaction mixture. 1.4 equivalents of 4,4'-dimethoxytriphenylmethyl chloride was added and the suspension formed was stirred for a duration of about 17.3 hours at 30° C. Samples from the reaction mixture were taken periodically (every 2 hours, 4 hours, etc.) and reaction products were characterized by HPLC.

yield. After 4 hours of reaction, 3-palmitoyl-amido-2-hydroxy-1-dimethoxytriphenylmethylether-propane was formed at 65.8% yield. The regioisomer impurity, 3-palmitoyl-amido-2-dimethoxytriphenylmethylether-1-hydroxy-propane was formed at 0.2% yield and the bis-tritylated compound increased to 11.2% yield. After 20 hours of reaction, 3-palmitoyl-amido-2-hydroxy-1-dimethoxytriphenylmethylether-propane was formed at 62.4% yield. The regioisomer impurity, 3-palmitoyl-amido-2-dimethoxytriphenylmethylether-1-hydroxy-propane was formed at 0.1%

TABLE 1

| Solvent | Bases | Additives | AP CMPD-A | AP DMTr-OH | AP DMTr-OMe | AP CMPD-B | AP CMPD B-Reg | AP Bis-DMTr | Sum AP DMTr-OR | CMPD-B/ Bis-DMTr | Sum AP known |
|---|---|---|---|---|---|---|---|---|---|---|---|
| THF | TMEDA | TBAF | 5.8 | 3.5 | 22.7 | 60.8 | 0.4 | 4.2 | 26.2 | 14.4 | 97.5 |
| THF | TEA | TBAF | 13.2 | 3.4 | 21.5 | 54.8 | 0.5 | 3.0 | 24.9 | 18.3 | 96.5 |
| THF | Proton Sponge | TBAF | 6.0 | 2.8 | 21.6 | 59.1 | 0.5 | 4.3 | 24.4 | 13.6 | 94.3 |
| Me—THF | TMEDA | TBAF | 0.1 | 5.0 | 23.9 | 53.7 | 0.0 | 13.3 | 28.9 | 4.0 | 96.1 |
| Me—THF | TEA | TBAF | 10.0 | 7.4 | 19.7 | 55.1 | 0.4 | 4.1 | 27.1 | 13.4 | 96.7 |
| Me—THF | Proton Sponge | TBAF | 23.7 | 3.9 | 18.5 | 45.8 | 0.5 | 2.8 | 22.4 | 16.3 | 95.1 |
| THF | TMEDA | MgO | 0.0 | 2.1 | 2.3 | 76.0 | 0.1 | 15.1 | 4.5 | 5.0 | 95.6 |
| THF | TEA | MgO | 0.0 | 2.3 | 6.2 | 50.3 | 0.0 | 35.1 | 8.6 | 1.4 | 94.0 |
| THF | Proton Sponge | MgO | 0.0 | 1.5 | 4.2 | 60.2 | 0.0 | 27.7 | 5.8 | 2.2 | 93.6 |
| Me—THF | TMEDA | MgO | 0.1 | 4.0 | 8.1 | 47.9 | 0.0 | 34.4 | 12.0 | 1.4 | 94.5 |
| Me—THF | TEA | MgO | 0.0 | 4.1 | 3.8 | 54.6 | 0.0 | 29.7 | 7.9 | 1.8 | 92.3 |
| THF | TMEDA | B(OH)3 | 0.0 | 32.7 | 1.0 | 61.1 | 2.1 | 0.9 | 33.7 | 66.4 | 97.8 |
| THF | TEA | B(OH)3 | 22.8 | 25.0 | 0.8 | 46.8 | 1.5 | 1.1 | 25.8 | 41.8 | 98.0 |
| THF | Proton Sponge | B(OH)3 | 33.8 | 14.2 | 0.4 | 41.7 | 0.3 | 3.5 | 14.7 | 12.1 | 93.9 |
| Me—THF | TMEDA | B(OH)3 | 62.2 | 11.3 | 0.5 | 22.2 | 0.7 | 0.7 | 11.8 | 29.7 | 97.6 |
| Me—THF | TEA | B(OH)3 | 32.0 | 20.2 | 0.7 | 40.9 | 1.1 | 2.5 | 20.9 | 16.2 | 97.5 |
| Me—THF | Proton Sponge | B(OH)3 | 0.8 | 28.0 | 1.0 | 51.7 | 0.2 | 12.3 | 29.0 | 4.2 | 94.0 |
| THF | TMEDA | | 0.0 | 1.6 | 4.9 | 63.5 | 0.0 | 25.0 | 6.6 | 2.5 | 95.0 |
| THF | TEA | | 0.0 | 1.9 | 4.8 | 55.1 | 0.0 | 32.1 | 6.7 | 1.7 | 93.9 |
| THF | Proton Sponge | | 0.0 | 1.1 | 6.7 | 50.7 | 0.0 | 34.7 | 7.8 | 1.5 | 93.2 |
| Me—THF | TMEDA | | 0.0 | 4.4 | 2.0 | 73.5 | 0.3 | 15.4 | 6.4 | 4.8 | 95.5 |
| Me—THF | TEA | | 0.0 | 4.1 | 2.4 | 58.9 | 0.1 | 30.1 | 6.5 | 2.0 | 95.6 |
| Me—THF | Proton Sponge | | 0.0 | 3.2 | 8.0 | 41.3 | 0.0 | 40.6 | 11.3 | 1.0 | 93.2 |

Example 3-Preparation of 3-palmitoyl-amido-2-hydroxy-1-dimethoxytriphenylmetylether-propane (Compound B) from 3-palmitoyl-amido-1,2-propanediol (Compound A) with methyl THF and TEA 3-palmitoyl-amido-1,2-propanediol was charged into a three-neck round bottom flask with methyl THF at 30° C. to produce a white suspension and stirred for 1 hour at 30° C. The flask was equipped with overhead stirring, a thermocouple, a nitrogen inlet and a glass stopper. 3.0 equivalents of triethylamine was added and was stirred for 0.5 hours at 30° C. To the white suspension, 1.4 equivalents of 4,4'-dimethoxytriphenylmethyl chloride was added all at once. The resulting yellow suspension was stirred at 30° C. for 23 hours. Analysis was done on samples at 2 hours, 4 hours, 20 hours, and 23 hours to confirm progression of the tritylation reaction and formation of any impurities (e.g., undesired regioisomer and bis-tritylated compound). After 2 hours of reaction, 3-palmitoyl-amido-2-hydroxy-1-dimethoxytriphenylmethylether-propane was formed at 63.2% yield. The regioisomer impurity, 3-palmitoyl-amido-2-dimethoxytriphenylmethylether-1-hydroxy-propane was formed at 0.4% yield and the bis-tritylated compound exhibited a 7.8% yield and the bis-tritylated compound increased to 16.6% yield. After 23 hours, 3-palmitoyl-amido-2-hydroxy-1-dimethoxytriphenylmethylether-propane was formed at 62.6% yield. The regioisomer impurity, 3-palmitoyl-amido-2-dimethoxytriphenylmethylether-1-hydroxy-propane was formed at 0.1% yield and the bis-tritylated compound remained at 16.6% yield.

Example 4-Preparation of 3-palmitoyl-amido-2-hydroxy-1-dimethoxytriphenylmethylether-propane (Comp[ound B) from 3-palmitoyl-amido-1,2-propanediol (Compound A) with methyl-THF and TEA and magnesium oxide 3-palmitoyl-amido-1,2-propanediol and 0.3 equivalents of magnesium oxide were charged into a three-neck round bottom flask with methyl THF at at 30° C. The flask was equipped with overhead stirring, a thermocouple, a nitrogen inlet and a glass stopper. The white suspension was stirred for 1 hour at 30° C. 3.0 equivalents of triethylamine was added and stirred for 0.5 hours at 30° C. 1.4 equivalents of 4,4'-dimethoxytriphenylmethyl chloride was added all at once. The resulting green-yellow suspension was stirred at 30° C. for 23 hours. Analysis was done on samples at 2 hours, 4 hours, 20 hours, and 23 hours to confirm progression of the tritylation reaction and formation of any impurities (e.g., undesired regioisomer and bis-tritylated compound). After 2 hours of reaction, 3-palmitoyl-amido-2-hydroxy-1-dimethoxytriphenylmethylether-propane was formed at 63.2% yield. The regioisomer impurity, 3-palmitoyl-amido-2-dimethoxytriphenylmethylether-1-hydroxy-propane was formed at 0.4% yield and the bis-tritylated compound exhibited a 7.7% yield. After 4 hours of reaction, 3-palmitoyl-amido-2-hydroxy-1-dimethoxytriphenylmethylether-propane was formed at 65.7% yield. The regioisomer impurity, 3-palmitoyl-amido-2-dimethoxytriphenylmethylether-1-hydroxy-propane was formed at 0.3% yield and the bis-tritylated compound increased to 11.0% yield. After 20 hours of reaction, 3-palmitoyl-amido-2-hydroxy-1-dimethoxytriphenylmethylether-propane was formed at 63.2% yield. The regioisomer impurity, 3-palmitoyl-amido-2-dimethoxytriphenylmethylether-1-hydroxy-propane was no longer present and the bis-tritylated compound increased to 16.7% yield. After 23 hours, 3-palmitoyl-amido-2-hydroxy-1-dimethoxytriphenylmethylether-propane was formed at 62.6% yield. The regioisomer impurity, 3-palmitoyl-amido-2-dimethoxytriphenylmethylether-1-hydroxy-propane was formed at 0.1% yield and the bis-tritylated compound increased slightly to 16.9% yield.

Example 5-Preparation of 3-palmitoyl-amido-2-hydroxy-1-dimethoxytriphenylmethylether-propane (Compound B) from 3-palmitoyl-amido-1,2-propanediol (Compound A) with methyl-THF and TEA and magnesium oxide and heating 3-palmitoyl-amido-1,2-propanediol, 0.3 equivalents of magnesium oxide and 3.0 equivalents of triethylamine were charged into a three-neck round bottom flask with methyl THF at ambient temperature. The flask was equipped with overhead stirring, a thermocouple, a nitrogen inlet and a glass stopper. The composition was heated to 48° C. to produce a white suspension and stirred for 1 hour at 48° C. The composition was further heated to 55° C. and stirred for another 1 hour. The reaction was again heated to 60° C. and stirred for another 30 minutes. The reaction was cooled to 30° C. over 70 minutes and to the resulting white suspension, 1.4 equivalents of 4,4'-dimethoxytriphenylmethyl chloride was added all at once. The resulting light green suspension was stirred at 30° C. for 23 hours. Analysis was done on samples at 2 hours, 4 hours, 20 hours, and 23 hours to confirm progression of the tritylation reaction and formation of any impurities (e.g., undesired regioisomer and bis-tritylated compound). After 2 hours of reaction, 3-palmitoyl-amido-2-hydroxy-1-dimethoxytriphenylmethylether-propane was formed at 67.0% yield. The regioisomer impurity, 3-palmitoyl-amido-2-dimethoxytriphenylmethylether-1-hydroxy-propane was formed at 0.2% yield and the bis-tritylated compound exhibited a 8.3% yield. After 4 hours of reaction, 3-palmitoyl-amido-2-hydroxy-1-dimethoxytriphenylmethylether-propane was formed at 66.2% yield. The regioisomer impurity, 3-palmitoyl-amido-2-dimethoxytriphenylmethylether-1-hydroxy-propane was formed at 0.1% yield and the bis-tritylated compound increased to 11.6% yield. After 20 hours of reaction, 3-palmitoyl-amido-2-hydroxy-1-dimethoxytriphenylmethylether-propane was formed at 63.2% yield. The regioisomer impurity, 3-palmitoyl-amido-2-dimethoxytriphenylmethylether-1-hydroxy-propane was no longer present and the bis-tritylated compound increased to 18.1% yield. After 23 hours, 3-palmitoyl-amido-2-hydroxy-1-dimethoxytriphenylmethylether-propane was formed at 63.0% yield. The regioisomer impurity, 3-palmitoyl-amido-2-dimethoxytriphenylmethylether-1-hydroxy-propane was no longer present and the bis-tritylated compound increased slightly to 18.2% yield.

Example 6—X-ray Crystallography of 3-palmitoyl-amido-2-hydroxy-1-dimethoxytriphenylmethylether-propane Single crystals of 3-palmitoyl-amido-2-hydroxy-1-dimethoxytriphenylmethylether-propane were produced by recrystallization of compositions of 3-palmitoyl-amido-2-hydroxy-1-dimethoxytriphenylmethylether-propane in various solvent and solvent mixtures. Single crystals formed from dichloromethane/pentane were used for X-ray diffraction studies.

X-ray diffraction was collected on single crystals in neat form at −100° C. A monoclinic plate-like specimen, approximate dimensions 0.080 mm×0.130 mm×0.130 mm, was used for the X-ray crystallographic analysis. The X-ray structure was studied using a Bruker D8 QUEST Single-crystal X-ray Diffractometer, equipped with high brightness IS 3.0 microfocus (50 kV×1 mA) for Cu radiation ($\lambda$=1.54178 Å) and with PHOTON II Charge-Integrating Pixel Array Detector of superior speed, sensitivity, and accuracy, was used for screening/evaluation of crystals and for diffraction data collection. Cryostream 800 low temperature device furnishes sample temperatures between 80 K and 500 K was used to cool crystals at 173K (−100° C.). Bruker APEX3 software suite including SHELXTL was for diffraction experiments for data collection and integration, and for solving, refining and displaying of structural results.

A total of 1346 frames were collected. The total exposure time was 12.76 hours. The frames were integrated with the Bruker SAINT software package using a narrow-frame algorithm. The integration of the data using a triclinic unit cell yielded a total of 30535 reflections to a maximum $\theta$ angle of 65.20° (0.85 Å resolution), of which 12077 were independent (average redundancy 2.528, completeness=96.7%, Rint=3.33%, Rsig=3.88%) and 10927 (90.48%) were greater than $2\sigma(F2)$. The final cell constants of a=8.6815(6) Å, b=12.9371(9) Å, c=32.676(2) Å, $\alpha$=83.787(3)°, $\beta$=87.487(3)°, $\gamma$=89.930(3)°, volume=3644.9 (4) $Å^3$, are based upon the refinement of the XYZ-centroids of 9845 reflections above 20 $\sigma(I)$ with 6.873°<2$\theta$<130.4°. Data were corrected for absorption effects using the Multi-Scan method (SADABS). The ratio of minimum to maximum apparent transmission was 0.853. The calculated minimum and maximum transmission coefficients (based on crystal size) are 0.9280 and 0.9550. The structure was solved and refined using the Bruker SHELXTL Software Package, using the space group P-1, with Z=4 for the formula unit, C40H57NO5. The final anisotropic full-matrix least-squares refinement on F2 with 838 variables converged at R1=11.45%, for the observed data and wR2=26.68% for all data. The goodness-of-fit was 1.106. The largest peak in the final difference electron density synthesis was 0.692 e-/$Å^3$ and the largest hole was −0.510 e-/$Å^3$ with an RMS deviation of 0.073 e-/$Å^3$. On the basis of the final model, the calculated density was 1.151 g/cm3. Table 2 provides atomic coordinates and equivalent isotropic atomic displacement parameters ($Å^2$) as determined from the crystal structure of 3-palmitoyl-amido-2-hydroxy-1-dimethoxytriphenylmethylether-propane. Table 3 provides the measured bond lengths (A) as determined from the crystal structure of 3-palmitoyl-amido-2-hydroxy-1-dimethoxytriphenylmethylether-propane. Table 4 provides the measured bond angles (°) as determined from the crystal structure of 3-palmitoyl-amido-2-hydroxy-1-dimethoxytriphenylmethylether-propane. Table 5 provides the measured torsion angles (°) as determined from the crystal structure of 3-palmitoyl-amido-2-hydroxy-1-dimethoxytriphenylmethylether-propane. Table 6 provides anisotropic atomic displacement parameters ($Å^2$) as determined from the crystal structure of 3-palmitoyl-amido-2-hydroxy-1-dimethoxytriphenylmethylether-propane. Table 7 provides the hydrogen atomic coordinates and isotropic atomic displacement parameters ($Å^2$) as determined from the crystal structure of 3-palmitoyl-amido-2-hydroxy-1-dimethoxytriphenylmethylether-propane.

FIG. 4A depicts an Oak Ridge Thermal Ellipsoid Plot (ORTEP)diagram of the two different conformations of 3-palmitoyl-amido-2-hydroxy-1-dimethoxytriphenylmethylether-propane determined by X-ray crystallography. Conformer A exhibits a linear conformation of 3-palmitoyl-amido-2-hydroxy-1-dimethoxytriphenylmethylether-propane. Conformer B exhibits a bent conformation of 3-palmitoyl-amido-2-hydroxy-1-dimethoxytriphenylmethylether-propane. FIG. 4B depicts a unit cell of a crystal of 3-palmitoyl-amido-2-hydroxy-1-dimethoxytriphenylmethylether-propane where each unit cell includes 4 molecules (2 molecules of conformer A and two molecules of conformer B) of 3-palmitoyl-amido-2-hydroxy-1-dimethoxytriphenylmethylether-propane. FIG. 4C depicts a view of crystal packing of 3-palmitoyl-amido-2-hydroxy-1-dimethoxytriphenylmethylether-propane along a first axis and FIG. 4D depicts crystal packing of 3-palmitoyl-amido-2-hydroxy-1-dimethoxytriphenylmethylether-propane along a second axis. FIG. 4E depicts the intermolecular hydrogen bonding between conformer A and conformer B along the second crystallographic axis.

TABLE 2

Atomic coordinates and equivalent isotropic atomic displacement parameters

| | x/a | y/b | z/c | U(eq) |
|---|---|---|---|---|
| C1A | 0.3510(10) | 0.7692(7) | 0.3604(3) | 0.089(3) |
| C2A | 0.2495(8) | 0.8404(5) | 0.3833(2) | 0.0613(17) |
| C3A | 0.3331(7) | 0.8953(5) | 0.4147(2) | 0.0547(15) |
| C4A | 0.2303(7) | 0.9690(5) | 0.43662(19) | 0.0543(15) |
| C5A | 0.3122(7) | 0.0278(5) | 0.4674(2) | 0.0573(16) |
| C6A | 0.2061(7) | 0.1025(5) | 0.48786(19) | 0.0561(16) |
| C7A | 0.2829(7) | 0.1618(5) | 0.5193(2) | 0.0571(16) |
| C8A | 0.1738(7) | 0.2369(5) | 0.5384(2) | 0.0564(16) |
| C9A | 0.2451(7) | 0.2973(5) | 0.57015(19) | 0.0560(16) |
| C10A | 0.1340(7) | 0.3721(5) | 0.58881(19) | 0.0557(16) |
| O1A | 0.8579(3) | 0.7210(3) | 0.75600(12) | 0.0408(9) |
| N1A | 0.0410(5) | 0.8405(4) | 0.75844(15) | 0.0504(13) |
| C11A | 0.2017(7) | 0.4325(5) | 0.62082(19) | 0.0531(15) |
| C12A | 0.0889(7) | 0.5070(5) | 0.63866(18) | 0.0515(15) |
| C13A | 0.1533(6) | 0.5644(4) | 0.67235(18) | 0.0471(13) |
| C14A | 0.0420(6) | 0.6406(4) | 0.68957(17) | 0.0458(13) |
| C15A | 0.1085(5) | 0.6886(4) | 0.72582(16) | 0.0371(11) |
| C16A | 0.9924(5) | 0.7525(4) | 0.74799(15) | 0.0343(11) |
| C17A | 0.9406(6) | 0.9132(5) | 0.7791(2) | 0.0557(16) |
| C18A | 0.0278(5) | 0.9735(4) | 0.80583(18) | 0.0400(12) |
| O2A | 0.1483(4) | 0.0319(3) | 0.78391(14) | 0.0563(11) |
| C19A | 0.9269(5) | 0.0537(4) | 0.82453(16) | 0.0347(11) |
| O3A | 0.7935(3) | 0.0018(2) | 0.84425(10) | 0.0305(7) |
| C20A | 0.6767(5) | 0.0702(3) | 0.85979(14) | 0.0278(10) |
| C21A | 0.7402(5) | 0.1203(3) | 0.89624(14) | 0.0264(9) |
| C22A | 0.8470(5) | 0.0650(4) | 0.92084(14) | 0.0302(10) |
| C23A | 0.8986(5) | 0.1026(4) | 0.95569(15) | 0.0343(11) |
| C24A | 0.8469(5) | 0.1983(4) | 0.96695(14) | 0.0303(10) |
| O4A | 0.9087(4) | 0.2306(3) | 0.00150(10) | 0.0428(9) |
| C25A | 0.8669(8) | 0.3313(5) | 0.01188(18) | 0.0574(16) |
| C26A | 0.7392(5) | 0.2523(4) | 0.94361(14) | 0.0294(10) |
| C27A | 0.6851(5) | 0.2136(3) | 0.90873(13) | 0.0265(9) |

TABLE 2-continued

Atomic coordinates and equivalent isotropic atomic displacement parameters

| | x/a | y/b | z/c | U(eq) |
|---|---|---|---|---|
| C28A | 0.6225(5) | 0.1445(3) | 0.82374(14) | 0.0269(10) |
| C29A | 0.5262(5) | 0.1041(4) | 0.79597(15) | 0.0321(10) |
| C30A | 0.4806(5) | 0.1635(4) | 0.76086(15) | 0.0360(11) |
| C31A | 0.5260(5) | 0.2661(4) | 0.75301(14) | 0.0333(11) |
| C32A | 0.5312(8) | 0.4222(5) | 0.70629(18) | 0.0560(16) |
| C33A | 0.6214(5) | 0.3089(4) | 0.77977(14) | 0.0327(10) |
| O5A | 0.4710(4) | 0.3205(3) | 0.71806(11) | 0.0440(9) |
| C34A | 0.6712(5) | 0.2460(3) | 0.81424(14) | 0.0304(10) |
| C35A | 0.5428(5) | 0.9986(3) | 0.87697(14) | 0.0267(9) |
| C36A | 0.4127(5) | 0.0424(4) | 0.89437(17) | 0.0407(12) |
| C37A | 0.2875(6) | 0.9821(4) | 0.90975(18) | 0.0464(14) |
| C38A | 0.2914(6) | 0.8750(4) | 0.90881(15) | 0.0383(12) |
| C39A | 0.4193(6) | 0.8308(4) | 0.89148(16) | 0.0375(11) |
| C40A | 0.5444(5) | 0.8916(3) | 0.87551(14) | 0.0301(10) |
| C1B | 0.8259(9) | 0.9773(5) | 0.3541(2) | 0.0705(19) |
| C2B | 0.8579(10) | 0.0767(6) | 0.3684(3) | 0.093(3) |
| C3B | 0.7945(8) | 0.1091(6) | 0.4062(2) | 0.0690(19) |
| C4B | 0.8239(8) | 0.2065(5) | 0.4211(2) | 0.0644(18) |
| C5B | 0.7582(9) | 0.2397(6) | 0.4589(3) | 0.084(3) |
| C6B | 0.7856(7) | 0.3380(5) | 0.4734(2) | 0.0600(17) |
| C7B | 0.7172(10) | 0.3726(6) | 0.5105(3) | 0.095(3) |
| C8B | 0.7422(8) | 0.4728(5) | 0.5245(2) | 0.0644(18) |
| C9B | 0.6756(10) | 0.5066(6) | 0.5618(3) | 0.091(3) |
| C10B | 0.6983(8) | 0.6065(5) | 0.5749(2) | 0.0678(19) |
| C11B | 0.6325(9) | 0.6422(6) | 0.6125(2) | 0.080(2) |
| C12B | 0.6576(9) | 0.7434(6) | 0.6246(2) | 0.076(2) |
| C13B | 0.6024(7) | 0.7803(5) | 0.6623(2) | 0.0595(17) |
| C14B | 0.6214(12) | 0.8837(6) | 0.6724(3) | 0.108(4) |
| C15B | 0.6000(8) | 0.9258(4) | 0.71007(18) | 0.0535(15) |
| C16B | 0.4896(5) | 0.8692(3) | 0.74247(15) | 0.0302(10) |
| O1B | 0.3551(4) | 0.8951(3) | 0.74538(15) | 0.0585(12) |
| N1B | 0.5490(4) | 0.7896(3) | 0.76518(12) | 0.0331(9) |
| C17B | 0.4546(9) | 0.7164(5) | 0.7920(2) | 0.071(2) |
| C18B | 0.5183(8) | 0.6233(4) | 0.8063(3) | 0.087(3) |
| O2B | 0.6309(4) | 0.5760(3) | 0.78120(13) | 0.0517(11) |
| C19B | 0.4253(5) | 0.5379(4) | 0.82776(16) | 0.0344(11) |
| O3B | 0.2917(3) | 0.5769(2) | 0.84798(10) | 0.0314(7) |
| C20B | 0.1761(5) | 0.5000(3) | 0.86421(14) | 0.0274(10) |
| C21B | 0.2428(5) | 0.4288(3) | 0.90012(14) | 0.0276(10) |
| C22B | 0.3474(5) | 0.4693(3) | 0.92516(15) | 0.0310(10) |
| C23B | 0.4017(5) | 0.4108(4) | 0.95886(15) | 0.0355(11) |
| C24B | 0.3528(5) | 0.3084(4) | 0.96926(14) | 0.0306(10) |
| O4B | 0.4172(4) | 0.2551(3) | 0.00264(10) | 0.0395(8) |
| C25B | 0.3830(8) | 0.1469(4) | 0.01037(19) | 0.0589(17) |
| C26B | 0.2454(5) | 0.2675(4) | 0.94524(14) | 0.0309(10) |
| C27B | 0.1891(5) | 0.3283(3) | 0.91125(14) | 0.0284(10) |
| C28B | 0.1200(5) | 0.4431(3) | 0.82883(14) | 0.0275(10) |
| C29B | 0.1884(5) | 0.3527(4) | 0.81682(15) | 0.0317(10) |
| C30B | 0.1415(5) | 0.3082(4) | 0.78236(15) | 0.0348(11) |
| C31B | 0.0272(5) | 0.3560(4) | 0.75873(15) | 0.0357(11) |
| O5B | 0.9746(4) | 0.3213(3) | 0.72353(12) | 0.0483(9) |
| C32B | 0.0491(8) | 0.2333(5) | 0.70900(19) | 0.0574(16) |
| C33B | 0.9574(6) | 0.4447(4) | 0.77055(16) | 0.0388(12) |
| C34B | 0.0021(6) | 0.4872(4) | 0.80505(15) | 0.0349(11) |
| C35B | 0.0431(5) | 0.5642(3) | 0.88157(14) | 0.0281(10) |
| C36B | 0.0391(5) | 0.6713(3) | 0.87462(15) | 0.0306(10) |
| C37B | 0.9152(6) | 0.7259(4) | 0.89021(16) | 0.0376(11) |
| C38B | 0.7944(6) | 0.6744(4) | 0.91274(16) | 0.0406(12) |
| C39B | 0.7992(6) | 0.5674(4) | 0.91935(18) | 0.0483(14) |
| C40B | 0.9210(6) | 0.5127(4) | 0.90414(17) | 0.0405(12) |

TABLE 3

Bond Lengths

| Bond | Length | Bond | Length |
|---|---|---|---|
| C1A-C2A | 1.509(9) | C1A-H1AA | 0.98 |
| C1A-H1AB | 0.98 | C1A-H1AC | 0.98 |
| C2A-C3A | 1.520(8) | C2A-H2AA | 0.99 |
| C2A-H2AB | 0.99 | C3A-C4A | 1.519(8) |
| C3A-H3AA | 0.99 | C3A-H3AB | 0.99 |

TABLE 3-continued

| Bond Lengths | | | |
|---|---|---|---|
| Bond | Length | Bond | Length |
| C4A-C5A | 1.525(8) | C4A-H4AA | 0.99 |
| C4A-H4AB | 0.99 | C5A-C6A | 1.521(8) |
| C5A-H5AA | 0.99 | C5A-H5AB | 0.99 |
| C6A-C7A | 1.522(8) | C6A-H6AA | 0.99 |
| C6A-H6AB | 0.99 | C7A-C8A | 1.519(8) |
| C7A-H7AA | 0.99 | C7A-H7AB | 0.99 |
| C8A-C9A | 1.519(8) | C8A-H8AA | 0.99 |
| C8A-H8AB | 0.99 | C9A-C10A | 1.520(8) |
| C9A-H9AA | 0.99 | C9A-H9AB | 0.99 |
| C10A-C11A | 1.511(8) | C10A-H10A | 0.99 |
| C10A-H10B | 0.99 | O1A-C16A | 1.244(6) |
| N1A-C16A | 1.299(6) | N1A-C17A | 1.478(6) |
| N1A-H1A | 0.88 | C11A-C12A | 1.516(8) |
| C11A-H11A | 0.99 | C11A-H11B | 0.99 |
| C12A-C13A | 1.519(8) | C12A-H12A | 0.99 |
| C12A-H12B | 0.99 | C13A-C14A | 1.514(7) |
| C13A-H13A | 0.99 | C13A-H13B | 0.99 |
| C14A-C15A | 1.530(7) | C14A-H14A | 0.99 |
| C14A-H14B | 0.99 | C15A-C16A | 1.512(6) |
| C15A-H15A | 0.99 | C15A-H15B | 0.99 |
| C17A-C18A | 1.466(8) | C17A-H17A | 0.99 |
| C17A-H17B | 0.99 | C18A-O2A | 1.413(6) |
| C18A-C19A | 1.519(6) | C18A-H18A | 1.0 |
| O2A-H2A | 0.84 | C19A-O3A | 1.432(5) |
| C19A-H19A | 0.99 | C19A-H19B | 0.99 |
| O3A-C20A | 1.456(5) | C20A-C28A | 1.528(6) |
| C20A-C35A | 1.535(6) | C20A-C21A | 1.539(6) |
| C21A-C27A | 1.393(6) | C21A-C22A | 1.399(6) |
| C22A-C23A | 1.378(7) | C22A-H22A | 0.95 |
| C23A-C24A | 1.397(7) | C23A-H23A | 0.95 |
| C24A-C26A | 1.374(6) | C24A-O4A | 1.376(6) |
| O4A-C25A | 1.423(7) | C25A-H25A | 0.98 |
| C25A-H25B | 0.98 | C25A-H25C | 0.98 |
| C26A-C27A | 1.393(6) | C26A-H26A | 0.95 |
| C27A-H27A | 0.95 | C28A-C34A | 1.378(6) |
| C28A-C29A | 1.402(6) | C29A-C30A | 1.383(7) |
| C29A-H29A | 0.95 | C30A-C31A | 1.380(7) |
| C30A-H30A | 0.95 | C31A-O5A | 1.378(6) |
| C31A-C33A | 1.388(7) | C32A-O5A | 1.424(7) |
| C32A-H32A | 0.98 | C32A-H32B | 0.98 |
| C32A-H32C | 0.98 | C33A-C34A | 1.401(7) |
| C33A-H33A | 0.95 | C34A-H34A | 0.95 |
| C35A-C36A | 1.390(6) | C35A-C40A | 1.390(6) |
| C36A-C37A | 1.383(7) | C36A-H36A | 0.95 |
| C37A-C38A | 1.391(7) | C37A-H37A | 0.95 |
| C38A-C39A | 1.376(7) | C38A-H38A | 0.95 |
| C39A-C40A | 1.391(6) | C39A-H39A | 0.95 |
| C40A-H40A | 0.95 | C1B-C2B | 1.447(9) |
| C1B-H1BA | 0.98 | C1B-H1BB | 0.98 |
| C1B-H1BC | 0.98 | C2B-C3B | 1.433(9) |
| C2B-H2B1 | 0.99 | C2B-H2B2 | 0.99 |
| C3B-C4B | 1.425(9) | C3B-H3B1 | 0.99 |
| C3B-H3B2 | 0.99 | C4B-C5B | 1.446(8) |
| C4B-H4B1 | 0.99 | C4B-H4B2 | 0.99 |
| C5B-C6B | 1.427(9) | C5B-H5B1 | 0.99 |
| C5B-H5B2 | 0.99 | C6B-C7B | 1.442(8) |
| C6B-H6B1 | 0.99 | C6B-H6B2 | 0.99 |
| C7B-C8B | 1.441(9) | C7B-H7B1 | 0.99 |
| C7B-H7B2 | 0.99 | C8B-C9B | 1.435(8) |
| C8B-H8B1 | 0.99 | C8B-H8B2 | 0.99 |
| C9B-C10B | 1.422(9) | C9B-H9B1 | 0.99 |
| C9B-H9B2 | 0.99 | C10B-C11B | 1.453(8) |
| C10B-H10C | 0.99 | C10B-H10D | 0.99 |
| C11B-C12B | 1.427(9) | C11B-H11C | 0.99 |
| C11B-H11D | 0.99 | C12B-C13B | 1.431(8) |
| C12B-H12C | 0.99 | C12B-H12D | 0.99 |
| C13B-C14B | 1.425(9) | C13B-H13C | 0.99 |
| C13B-H13D | 0.99 | C14B-C15B | 1.403(9) |
| C14B-H14C | 0.99 | C14B-H14D | 0.99 |
| C15B-C16B | 1.523(7) | C15B-H15C | 0.99 |
| C15B-H15D | 0.99 | C16B-O1B | 1.217(6) |
| C16B-N1B | 1.321(6) | N1B-C17B | 1.449(7) |
| N1B-H1B | 0.88 | C17B-C18B | 1.368(8) |
| C17B-H17C | 0.99 | C17B-H17D | 0.99 |
| C18B-O2B | 1.427(6) | C18B-C19B | 1.466(7) |
| C18B-H18B | 1.0 | O2B-H2BA | 0.98(7) |

TABLE 3-continued

| Bond Lengths | | | |
|---|---|---|---|
| Bond | Length | Bond | Length |
| C19B-O3B | 1.428(5) | C19B-H19C | 0.99 |
| C19B-H19D | 0.99 | O3B-C20B | 1.456(5) |
| C20B-C28B | 1.533(6) | C20B-C21B | 1.544(6) |
| C20B-C35B | 1.545(6) | C21B-C27B | 1.387(6) |
| C21B-C22B | 1.389(7) | C22B-C23B | 1.369(7) |
| C22B-H22B | 0.95 | C23B-C24B | 1.393(7) |
| C23B-H23B | 0.95 | C24B-O4B | 1.366(6) |
| C24B-C26B | 1.386(7) | O4B-C25B | 1.424(7) |
| C25B-H25D | 0.98 | C25B-H25E | 0.98 |
| C25B-H25F | 0.98 | C26B-C27B | 1.396(6) |
| C26B-H26B | 0.95 | C27B-H27B | 0.95 |
| C28B-C34B | 1.397(7) | C28B-C29B | 1.397(6) |
| C29B-C30B | 1.395(7) | C29B-H29B | 0.95 |
| C30B-C31B | 1.387(7) | C30B-H30B | 0.95 |
| C31B-O5B | 1.375(6) | C31B-C33B | 1.382(7) |
| O5B-C32B | 1.424(7) | C32B-H32D | 0.98 |
| C32B-H32E | 0.98 | C32B-H32F | 0.98 |
| C33B-C34B | 1.377(7) | C33B-H33B | 0.95 |
| C34B-H34B | 0.95 | C35B-C36B | 1.379(6) |
| C35B-C40B | 1.392(6) | C36B-C37B | 1.394(6) |
| C36B-H36B | 0.95 | C37B-C38B | 1.383(7) |
| C37B-H37B | 0.95 | C38B-C39B | 1.379(7) |
| C38B-H38B | 0.95 | C39B-C40B | 1.376(7) |
| C39B-H39B | 0.95 | C40B-H40B | 0.95 |

TABLE 4

| Bond Angles | | | |
|---|---|---|---|
| Bond | Angle (°) | Bond | Angle (°) |
| C2A-C1A-H1AA | 109.5 | C2A-C1A-H1AB | 109.5 |
| H1AA-C1A-H1AB | 109.5 | C2A-C1A-H1AC | 109.5 |
| H1AA-C1A-H1AC | 109.5 | H1AB-C1A-H1AC | 109.5 |
| C1A-C2A-C3A | 113.9(6) | C1A-C2A-H2AA | 108.8 |
| C3A-C2A-H2AA | 108.8 | C1A-C2A-H2AB | 108.8 |
| C3A-C2A-H2AB | 108.8 | H2AA-C2A-H2AB | 107.7 |
| C4A-C3A-C2A | 113.1(5) | C4A-C3A-H3AA | 108.9 |
| C2A-C3A-H3AA | 108.9 | C4A-C3A-H3AB | 108.9 |
| C2A-C3A-H3AB | 108.9 | H3AA-C3A-H3AB | 107.8 |
| C3A-C4A-C5A | 114.4(5) | C3A-C4A-H4AA | 108.7 |
| C5A-C4A-H4AA | 108.7 | C3A-C4A-H4AB | 108.7 |
| C5A-C4A-H4AB | 108.7 | H4AA-C4A-H4AB | 107.6 |
| C6A-C5A-C4A | 112.6(5) | C6A-C5A-H5AA | 109.1 |
| C4A-C5A-H5AA | 109.1 | C6A-C5A-H5AB | 109.1 |
| C4A-C5A-H5AB | 109.1 | H5AA-C5A-H5AB | 107.8 |
| C5A-C6A-C7A | 114.3(5) | C5A-C6A-H6AA | 108.7 |
| C7A-C6A-H6AA | 108.7 | C5A-C6A-H6AB | 108.7 |
| C7A-C6A-H6AB | 108.7 | H6AA-C6A-H6AB | 107.6 |
| C8A-C7A-C6A | 112.6(5) | C8A-C7A-H7AA | 109.1 |
| C6A-C7A-H7AA | 109.1 | C8A-C7A-H7AB | 109.1 |
| C6A-C7A-H7AB | 109.1 | H7AA-C7A-H7AB | 107.8 |
| C9A-C8A-C7A | 114.5(5) | C9A-C8A-H8AA | 108.6 |
| C7A-C8A-H8AA | 108.6 | C9A-C8A-H8AB | 108.6 |
| C7A-C8A-H8AB | 108.6 | H8AA-C8A-H8AB | 107.6 |
| C8A-C9A-C10A | 113.6(5) | C8A-C9A-H9AA | 108.8 |
| C10A-C9A-H9AA | 108.8 | C8A-C9A-H9AB | 108.8 |
| C10A-C9A-H9AB | 108.8 | H9AA-C9A-H9AB | 107.7 |
| C11A-C10A-C9A | 114.7(5) | C11A-C10A-H10A | 108.6 |
| C9A-C10A-H10A | 108.6 | C11A-C10A-H10B | 108.6 |
| C9A-C10A-H10B | 108.6 | H10A-C10A-H10B | 107.6 |
| C16A-N1A-C17A | 123.2(4) | C16A-N1A-H1A | 118.4 |
| C17A-N1A-H1A | 118.4 | C10A-C11A-C12A | 113.6(5) |
| C10A-C11A-H11A | 108.8 | C12A-C11A-H11A | 108.8 |
| C10A-C11A-H11B | 108.8 | C12A-C11A-H11B | 108.8 |
| H11A-C11A-H11B | 107.7 | C11A-C12A-C13A | 114.0(5) |
| C11A-C12A-H12A | 108.7 | C13A-C12A-H12A | 108.7 |
| C11A-C12A-H12B | 108.7 | C13A-C12A-H12B | 108.7 |
| H12A-C12A-H12B | 107.6 | C14A-C13A-C12A | 114.1(5) |
| C14A-C13A-H13A | 108.7 | C12A-C13A-H13A | 108.7 |
| C14A-C13A-H13B | 108.7 | C12A-C13A-H13B | 108.7 |
| H13A-C13A-H13B | 107.6 | C13A-C14A-C15A | 111.5(5) |
| C13A-C14A-H14A | 109.3 | C15A-C14A-H14A | 109.3 |

TABLE 4-continued

| Bond Angles | | | |
|---|---|---|---|
| Bond | Angle (°) | Bond | Angle (°) |
| C13A-C14A-H14B | 109.3 | C15A-C14A-H14B | 109.3 |
| H14A-C14A-H14B | 108.0 | C16A-C15A-C14A | 113.2(4) |
| C16A-C15A-H15A | 108.9 | C14A-C15A-H15A | 108.9 |
| C16A-C15A-H15B | 108.9 | C14A-C15A-H15B | 108.9 |
| H15A-C15A-H15B | 107.8 | O1A-C16A-N1A | 122.3(4) |
| O1A-C16A-C15A | 121.1(4) | N1A-C16A-C15A | 116.6(4) |
| C18A-C17A-N1A | 111.6(4) | C18A-C17A-H17A | 109.3 |
| N1A-C17A-H17A | 109.3 | C18A-C17A-H17B | 109.3 |
| N1A-C17A-H17B | 109.3 | H17A-C17A-H17B | 108.0 |
| O2A-C18A-C17A | 112.2(5) | O2A-C18A-C19A | 104.7(4) |
| C17A-C18A-C19A | 111.5(4) | O2A-C18A-H18A | 109.4 |
| C17A-C18A-H18A | 109.4 | C19A-C18A-H18A | 109.4 |
| C18A-O2A-H2A | 109.5 | O3A-C19A-C18A | 108.3(3) |
| O3A-C19A-H19A | 110.0 | C18A-C19A-H19A | 110.0 |
| O3A-C19A-H19B | 110.0 | C18A-C19A-H19B | 110.0 |
| H19A-C19A-H19B | 108.4 | C19A-O3A-C20A | 114.8(3) |
| O3A-C20A-C28A | 108.6(3) | O3A-C20A-C35A | 105.4(3) |
| C28A-C20A-C35A | 109.4(4) | O3A-C20A-C21A | 109.0(3) |
| C28A-C20A-C21A | 116.5(4) | C35A-C20A-C21A | 107.3(3) |
| C27A-C21A-C22A | 117.6(4) | C27A-C21A-C20A | 123.2(4) |
| C22A-C21A-C20A | 118.8(4) | C23A-C22A-C21A | 121.2(4) |
| C23A-C22A-H22A | 119.4 | C21A-C22A-H22A | 119.4 |
| C22A-C23A-C24A | 120.5(4) | C22A-C23A-H23A | 119.8 |
| C24A-C23A-H23A | 119.8 | C26A-C24A-O4A | 124.9(4) |
| C26A-C24A-C23A | 118.9(4) | O4A-C24A-C23A | 116.1(4) |
| C24A-O4A-C25A | 117.3(4) | O4A-C25A-H25A | 109.5 |
| O4A-C25A-H25B | 109.5 | H25A-C25A-H25B | 109.5 |
| O4A-C25A-H25C | 109.5 | H25A-C25A-H25C | 109.5 |
| H25B-C25A-H25C | 109.5 | C24A-C26A-C27A | 120.6(4) |
| C24A-C26A-H26A | 119.7 | C27A-C26A-H26A | 119.7 |
| C21A-C27A-C26A | 121.0(4) | C21A-C27A-H27A | 119.5 |
| C26A-C27A-H27A | 119.5 | C34A-C28A-C29A | 117.0(4) |
| C34A-C28A-C20A | 125.2(4) | C29A-C28A-C20A | 117.6(4) |
| C30A-C29A-C28A | 121.6(4) | C30A-C29A-H29A | 119.2 |
| C28A-C29A-H29A | 119.2 | C31A-C30A-C29A | 120.1(4) |
| C31A-C30A-H30A | 120.0 | C29A-C30A-H30A | 120.0 |
| O5A-C31A-C30A | 116.2(4) | O5A-C31A-C33A | 123.9(4) |
| C30A-C31A-C33A | 119.9(4) | O5A-C32A-H32A | 109.5 |
| O5A-C32A-H32B | 109.5 | H32A-C32A-H32B | 109.5 |
| O5A-C32A-H32C | 109.5 | H32A-C32A-H32C | 109.5 |
| H32B-C32A-H32C | 109.5 | C31A-C33A-C34A | 118.9(4) |
| C31A-C33A-H33A | 120.5 | C34A-C33A-H33A | 120.5 |
| C31A-O5A-C32A | 117.4(4) | C28A-C34A-C33A | 122.3(4) |
| C28A-C34A-H34A | 118.8 | C33A-C34A-H34A | 118.8 |
| C36A-C35A-C40A | 118.1(4) | C36A-C35A-C20A | 118.8(4) |
| C40A-C35A-C20A | 123.1(4) | C37A-C36A-C35A | 121.4(5) |
| C37A-C36A-H36A | 119.3 | C35A-C36A-H36A | 119.3 |
| C36A-C37A-C38A | 120.0(5) | C36A-C37A-H37A | 120.0 |
| C38A-C37A-H37A | 120.0 | C39A-C38A-C37A | 119.1(4) |
| C39A-C38A-H38A | 120.5 | C37A-C38A-H38A | 120.5 |
| C38A-C39A-C40A | 120.9(5) | C38A-C39A-H39A | 119.5 |
| C40A-C39A-H39A | 119.5 | C35A-C40A-C39A | 120.5(4) |
| C35A-C40A-H40A | 119.8 | C39A-C40A-H40A | 119.8 |
| C2B-C1B-H1BA | 109.5 | C2B-C1B-H1BB | 109.5 |
| H1BA-C1B-H1BB | 109.5 | C2B-C1B-H1BC | 109.5 |
| H1BA-C1B-H1BC | 109.5 | H1BB-C1B-H1BC | 109.5 |
| C3B-C2B-C1B | 124.0(7) | C3B-C2B-H2B1 | 106.3 |
| C1B-C2B-H2B1 | 106.3 | C3B-C2B-H2B2 | 106.3 |
| C1B-C2B-H2B2 | 106.3 | H2B1-C2B-H2B2 | 106.4 |
| C4B-C3B-C2B | 125.2(6) | C4B-C3B-H3B1 | 106.0 |
| C2B-C3B-H3B1 | 106.0 | C4B-C3B-H3B2 | 106.0 |
| C2B-C3B-H3B2 | 106.0 | H3B1-C3B-H3B2 | 106.3 |
| C3B-C4B-C5B | 125.2(6) | C3B-C4B-H4B1 | 106.0 |
| C5B-C4B-H4B1 | 106.0 | C3B-C4B-H4B2 | 106.0 |
| C5B-C4B-H4B2 | 106.0 | H4B1-C4B-H4B2 | 106.3 |
| C6B-C5B-C4B | 125.1(6) | C6B-C5B-H5B1 | 106.0 |
| C4B-C5B-H5B1 | 106.0 | C6B-C5B-H5B2 | 106.0 |
| C4B-C5B-H5B2 | 106.0 | H5B1-C5B-H5B2 | 106.3 |
| C5B-C6B-C7B | 125.3(6) | C5B-C6B-H6B1 | 106.0 |
| C7B-C6B-H6B1 | 106.0 | C5B-C6B-H6B2 | 106.0 |
| C7B-C6B-H6B2 | 106.0 | H6B1-C6B-H6B2 | 106.3 |
| C8B-C7B-C6B | 125.2(6) | C8B-C7B-H7B1 | 106.0 |
| C6B-C7B-H7B1 | 106.0 | C8B-C7B-H7B2 | 106.0 |
| C6B-C7B-H7B2 | 106.0 | H7B1-C7B-H7B2 | 106.3 |
| C9B-C8B-C7B | 125.1(6) | C9B-C8B-H8B1 | 106.0 |
| C7B-C8B-H8B1 | 106.0 | C9B-C8B-H8B2 | 106.0 |

TABLE 4-continued

| Bond Angles | | | |
|---|---|---|---|
| Bond | Angle (°) | Bond | Angle (°) |
| C7B-C8B-H8B2 | 106.0 | H8B1-C8B-H8B2 | 106.3 |
| C10B-C9B-C8B | 124.8(6) | C10B-C9B-H9B1 | 106.1 |
| C8B-C9B-H9B1 | 106.1 | C10B-C9B-H9B2 | 106.1 |
| C8B-C9B-H9B2 | 106.1 | H9B1-C9B-H9B2 | 106.3 |
| C9B-C10B-C11B | 125.7(6) | C9B-C10B-H10C | 105.9 |
| C11B-C10B-H10C | 105.9 | C9B-C10B-H10D | 105.9 |
| C11B-C10B-H10D | 105.9 | H10C-C10B-H10D | 106.2 |
| C12B-C11B-C10B | 124.0(6) | C12B-C11B-H11C | 106.3 |
| C10B-C11B-H11C | 106.3 | C12B-C11B-H11D | 106.3 |
| C10B-C11B-H11D | 106.3 | H11C-C11B-H11D | 106.4 |
| C11B-C12B-C13B | 126.1(6) | C11B-C12B-H12C | 105.8 |
| C13B-C12B-H12C | 105.8 | C11B-C12B-H12D | 105.8 |
| C13B-C12B-H12D | 105.8 | H12C-C12B-H12D | 106.2 |
| C14B-C13B-C12B | 124.8(6) | C14B-C13B-H13C | 106.1 |
| C12B-C13B-H13C | 106.1 | C14B-C13B-H13D | 106.1 |
| C12B-C13B-H13D | 106.1 | H13C-C13B-H13D | 106.3 |
| C15B-C14B-C13B | 130.9(6) | C15B-C14B-H14C | 104.5 |
| C13B-C14B-H14C | 104.5 | C15B-C14B-H14D | 104.5 |
| C13B-C14B-H14D | 104.5 | H14C-C14B-H14D | 105.7 |
| C14B-C15B-C16B | 117.5(5) | C14B-C15B-H15C | 107.9 |
| C16B-C15B-H15C | 107.9 | C14B-C15B-H15D | 107.9 |
| C16B-C15B-H15D | 107.9 | H15C-C15B-H15D | 107.2 |
| O1B-C16B-N1B | 123.8(4) | O1B-C16B-C15B | 120.8(5) |
| N1B-C16B-C15B | 115.4(4) | C16B-N1B-C17B | 122.4(4) |
| C16B-N1B-H1B | 118.8 | C17B-N1B-H1B | 118.8 |
| C18B-C17B-N1B | 118.3(5) | C18B-C17B-H17C | 107.7 |
| N1B-C17B-H17C | 107.7 | C18B-C17B-H17D | 107.7 |
| N1B-C17B-H17D | 107.7 | H17C-C17B-H17D | 107.1 |
| C17B-C18B-O2B | 119.8(6) | C17B-C18B-C19B | 122.1(5) |
| O2B-C18B-C19B | 106.1(5) | C17B-C18B-H18B | 101.7 |
| O2B-C18B-H18B | 101.7 | C19B-C18B-H18B | 101.7 |
| C18B-O2B-H2BA | 109.5 | O3B-C19B-C18B | 110.8(4) |
| O3B-C19B-H19C | 109.5 | C18B-C19B-H19C | 109.5 |
| O3B-C19B-H19D | 109.5 | C18B-C19B-H19D | 109.5 |
| H19C-C19B-H19D | 108.1 | C19B-O3B-C20B | 116.1(3) |
| O3B-C20B-C28B | 109.1(3) | O3B-C20B-C21B | 109.2(3) |
| C28B-C20B-C21B | 114.8(3) | O3B-C20B-C35B | 104.6(3) |
| C28B-C20B-C35B | 109.9(4) | C21B-C20B-C35B | 108.6(4) |
| C27B-C21B-C22B | 118.1(4) | C27B-C21B-C20B | 122.1(4) |
| C22B-C21B-C20B | 119.5(4) | C23B-C22B-C21B | 121.3(4) |
| C23B-C22B-H22B | 119.4 | C21B-C22B-H22B | 119.4 |
| C22B-C23B-C24B | 120.9(4) | C22B-C23B-H23B | 119.6 |
| C24B-C23B-H23B | 119.6 | O4B-C24B-C26B | 124.8(4) |
| O4B-C24B-C23B | 116.6(4) | C26B-C24B-C23B | 118.6(4) |
| C24B-O4B-C25B | 117.0(4) | O4B-C25B-H25D | 109.5 |
| O4B-C25B-H25E | 109.5 | H25D-C25B-H25E | 109.5 |
| O4B-C25B-H25F | 109.5 | H25D-C25B-H25F | 109.5 |
| H25E-C25B-H25F | 109.5 | C24B-C26B-C27B | 120.1(4) |
| C24B-C26B-H26B | 119.9 | C27B-C26B-H26B | 119.9 |
| C21B-C27B-C26B | 121.0(4) | C21B-C27B-H27B | 119.5 |
| C26B-C27B-H27B | 119.5 | C34B-C28B-C29B | 117.4(4) |
| C34B-C28B-C20B | 118.9(4) | C29B-C28B-C20B | 123.5(4) |
| C30B-C29B-C28B | 121.5(4) | C30B-C29B-H29B | 119.3 |
| C28B-C29B-H29B | 119.3 | C31B-C30B-C29B | 119.5(4) |
| C31B-C30B-H30B | 120.2 | C29B-C30B-H30B | 120.2 |
| O5B-C31B-C33B | 115.6(4) | O5B-C31B-C30B | 124.9(4) |
| C33B-C31B-C30B | 119.5(5) | C31B-O5B-C32B | 117.5(4) |
| O5B-C32B-H32D | 109.5 | O5B-C32B-H32E | 109.5 |
| H32D-C32B-H32E | 109.5 | O5B-C32B-H32F | 109.5 |
| H32D-C32B-H32F | 109.5 | H32E-C32B-H32F | 109.5 |
| C34B-C33B-C31B | 120.7(5) | C34B-C33B-H33B | 119.7 |
| C31B-C33B-H33B | 119.7 | C33B-C34B-C28B | 121.3(4) |
| C33B-C34B-H34B | 119.3 | C28B-C34B-H34B | 119.3 |
| C36B-C35B-C40B | 118.6(4) | C36B-C35B-C20B | 122.2(4) |
| C40B-C35B-C20B | 119.2(4) | C35B-C36B-C37B | 120.2(4) |
| C35B-C36B-H36B | 119.9 | C37B-C36B-H36B | 119.9 |
| C38B-C37B-C36B | 121.0(4) | C38B-C37B-H37B | 119.5 |
| C36B-C37B-H37B | 119.5 | C39B-C38B-C37B | 118.3(4) |
| C39B-C38B-H38B | 120.8 | C37B-C38B-H38B | 120.8 |
| C40B-C39B-C38B | 121.2(5) | C40B-C39B-H39B | 119.4 |
| C38B-C39B-H39B | 119.4 | C39B-C40B-C35B | 120.7(5) |
| C39B-C40B-H40B | 119.6 | C35B-C40B-H40B | 119.6 |

TABLE 5

Torsion Angles

| Bond | Angle (°) | Bond | Angle (°) |
|---|---|---|---|
| C2A-C1A-H1AA | 109.5 | C2A-C1A-H1AB | 109.5 |
| H1AA-C1A-H1AB | 109.5 | C2A-C1A-H1AC | 109.5 |
| H1AA-C1A-H1AC | 109.5 | H1AB-C1A-H1AC | 109.5 |
| C1A-C2A-C3A | 113.9(6) | C1A-C2A-H2AA | 108.8 |
| C3A-C2A-H2AA | 108.8 | C1A-C2A-H2AB | 108.8 |
| C3A-C2A-H2AB | 108.8 | H2AA-C2A-H2AB | 107.7 |
| C4A-C3A-C2A | 113.1(5) | C4A-C3A-H3AA | 108.9 |
| C2A-C3A-H3AA | 108.9 | C4A-C3A-H3AB | 108.9 |
| C2A-C3A-H3AB | 108.9 | H3AA-C3A-H3AB | 107.8 |
| C3A-C4A-C5A | 114.4(5) | C3A-C4A-H4AA | 108.7 |
| C5A-C4A-H4AA | 108.7 | C3A-C4A-H4AB | 108.7 |
| C5A-C4A-H4AB | 108.7 | H4AA-C4A-H4AB | 107.6 |
| C6A-C5A-C4A | 112.6(5) | C6A-C5A-H5AA | 109.1 |
| C4A-C5A-H5AA | 109.1 | C6A-C5A-H5AB | 109.1 |
| C4A-C5A-H5AB | 109.1 | H5AA-C5A-H5AB | 107.8 |
| C5A-C6A-C7A | 114.3(5) | C5A-C6A-H6AA | 108.7 |
| C7A-C6A-H6AA | 108.7 | C5A-C6A-H6AB | 108.7 |
| C7A-C6A-H6AB | 108.7 | H6AA-C6A-H6AB | 107.6 |
| C8A-C7A-C6A | 112.6(5) | C8A-C7A-H7AA | 109.1 |
| C6A-C7A-H7AA | 109.1 | C8A-C7A-H7AB | 109.1 |
| C6A-C7A-H7AB | 109.1 | H7AA-C7A-H7AB | 107.8 |
| C9A-C8A-C7A | 114.5(5) | C9A-C8A-H8AA | 108.6 |
| C7A-C8A-H8AA | 108.6 | C9A-C8A-H8AB | 108.6 |
| C7A-C8A-H8AB | 108.6 | H8AA-C8A-H8AB | 107.6 |
| C8A-C9A-C10A | 113.6(5) | C8A-C9A-H9AA | 108.8 |
| C10A-C9A-H9AA | 108.8 | C8A-C9A-H9AB | 108.8 |
| C10A-C9A-H9AB | 108.8 | H9AA-C9A-H9AB | 107.7 |
| C11A-C10A-C9A | 114.7(5) | C11A-C10A-H10A | 108.6 |
| C9A-C10A-H10A | 108.6 | C11A-C10A-H10B | 108.6 |
| C9A-C10A-H10B | 108.6 | H10A-C10A-H10B | 107.6 |
| C16A-N1A-C17A | 123.2(4) | C16A-N1A-H1A | 118.4 |
| C17A-N1A-H1A | 118.4 | C10A-C11A-C12A | 113.6(5) |
| C10A-C11A-H11A | 108.8 | C12A-C11A-H11A | 108.8 |
| C10A-C11A-H11B | 108.8 | C12A-C11A-H11B | 108.8 |
| H11A-C11A-H11B | 107.7 | C11A-C12A-C13A | 114.0(5) |
| C11A-C12A-H12A | 108.7 | C13A-C12A-H12A | 108.7 |
| C11A-C12A-H12B | 108.7 | C13A-C12A-H12B | 108.7 |
| H12A-C12A-H12B | 107.6 | C14A-C13A-C12A | 114.1(5) |
| C14A-C13A-H13A | 108.7 | C12A-C13A-H13A | 108.7 |
| C14A-C13A-H13B | 108.7 | C12A-C13A-H13B | 108.7 |
| H13A-C13A-H13B | 107.6 | C13A-C14A-C15A | 111.5(5) |
| C13A-C14A-H14A | 109.3 | C15A-C14A-H14A | 109.3 |
| C13A-C14A-H14B | 109.3 | C15A-C14A-H14B | 109.3 |
| H14A-C14A-H14B | 108.0 | C16A-C15A-C14A | 113.2(4) |
| C16A-C15A-H15A | 108.9 | C14A-C15A-H15A | 108.9 |
| C16A-C15A-H15B | 108.9 | C14A-C15A-H15B | 108.9 |
| H15A-C15A-H15B | 107.8 | O1A-C16A-N1A | 122.3(4) |
| O1A-C16A-C15A | 121.1(4) | N1A-C16A-C15A | 116.6(4) |
| C18A-C17A-N1A | 111.6(4) | C18A-C17A-H17A | 109.3 |
| N1A-C17A-H17A | 109.3 | C18A-C17A-H17B | 109.3 |
| N1A-C17A-H17B | 109.3 | H17A-C17A-H17B | 108.0 |
| O2A-C18A-C17A | 112.2(5) | O2A-C18A-C19A | 104.7(4) |
| C17A-C18A-C19A | 111.5(4) | O2A-C18A-H18A | 109.4 |
| C17A-C18A-H18A | 109.4 | C19A-C18A-H18A | 109.4 |
| C18A-O2A-H2A | 109.5 | O3A-C19A-C18A | 108.3(3) |
| O3A-C19A-H19A | 110.0 | C18A-C19A-H19A | 110.0 |
| O3A-C19A-H19B | 110.0 | C18A-C19A-H19B | 110.0 |
| H19A-C19A-H19B | 108.4 | C19A-O3A-C20A | 114.8(3) |
| O3A-C20A-C28A | 108.6(3) | O3A-C20A-C35A | 105.4(3) |
| C28A-C20A-C35A | 109.4(4) | O3A-C20A-C21A | 109.0(3) |
| C28A-C20A-C21A | 116.5(4) | C35A-C20A-C21A | 107.3(3) |
| C27A-C21A-C22A | 117.6(4) | C27A-C21A-C20A | 123.2(4) |
| C22A-C21A-C20A | 118.8(4) | C23A-C22A-C21A | 121.2(4) |
| C23A-C22A-H22A | 119.4 | C21A-C22A-H22A | 119.4 |
| C22A-C23A-C24A | 120.5(4) | C22A-C23A-H23A | 119.8 |
| C24A-C23A-H23A | 119.8 | C26A-C24A-O4A | 124.9(4) |
| C26A-C24A-C23A | 118.9(4) | O4A-C24A-C23A | 116.1(4) |
| C24A-O4A-C25A | 117.3(4) | O4A-C25A-H25A | 109.5 |
| O4A-C25A-H25B | 109.5 | H25A-C25A-H25B | 109.5 |
| O4A-C25A-H25C | 109.5 | H25A-C25A-H25C | 109.5 |
| H25B-C25A-H25C | 109.5 | C24A-C26A-C27A | 120.6(4) |
| C24A-C26A-H26A | 119.7 | C27A-C26A-H26A | 119.7 |
| C21A-C27A-C26A | 121.0(4) | C21A-C27A-H27A | 119.5 |
| C26A-C27A-H27A | 119.5 | C34A-C28A-C29A | 117.0(4) |
| C34A-C28A-C20A | 125.2(4) | C29A-C28A-C20A | 117.6(4) |
| C30A-C29A-C28A | 121.6(4) | C30A-C29A-H29A | 119.2 |

TABLE 5-continued

Torsion Angles

| Bond | Angle (°) | Bond | Angle (°) |
|---|---|---|---|
| C28A-C29A-H29A | 119.2 | C31A-C30A-C29A | 120.1(4) |
| C31A-C30A-H30A | 120.0 | C29A-C30A-H30A | 120.0 |
| O5A-C31A-C30A | 116.2(4) | O5A-C31A-C33A | 123.9(4) |
| C30A-C31A-C33A | 119.9(4) | O5A-C32A-H32A | 109.5 |
| O5A-C32A-H32B | 109.5 | H32A-C32A-H32B | 109.5 |
| O5A-C32A-H32C | 109.5 | H32A-C32A-H32C | 109.5 |
| H32B-C32A-H32C | 109.5 | C31A-C33A-C34A | 118.9(4) |
| C31A-C33A-H33A | 120.5 | C34A-C33A-H33A | 120.5 |
| C31A-O5A-C32A | 117.4(4) | C28A-C34A-C33A | 122.3(4) |
| C28A-C34A-H34A | 118.8 | C33A-C34A-H34A | 118.8 |
| C36A-C35A-C40A | 118.1(4) | C36A-C35A-C20A | 118.8(4) |
| C40A-C35A-C20A | 123.1(4) | C37A-C36A-C35A | 121.4(5) |
| C37A-C36A-H36A | 119.3 | C35A-C36A-H36A | 119.3 |
| C36A-C37A-C38A | 120.0(5) | C36A-C37A-H37A | 120.0 |
| C38A-C37A-H37A | 120.0 | C39A-C38A-C37A | 119.1(4) |
| C39A-C38A-H38A | 120.5 | C37A-C38A-H38A | 120.5 |
| C38A-C39A-C40A | 120.9(5) | C38A-C39A-H39A | 119.5 |
| C40A-C39A-H39A | 119.5 | C35A-C40A-C39A | 120.5(4) |
| C35A-C40A-H40A | 119.8 | C39A-C40A-H40A | 119.8 |
| C2B-C1B-H1BA | 109.5 | C2B-C1B-H1BB | 109.5 |
| H1BA-C1B-H1BB | 109.5 | C2B-C1B-H1BC | 109.5 |
| H1BA-C1B-H1BC | 109.5 | H1BB-C1B-H1BC | 109.5 |
| C3B-C2B-C1B | 124.0(7) | C3B-C2B-H2B1 | 106.3 |
| C1B-C2B-H2B1 | 106.3 | C3B-C2B-H2B2 | 106.3 |
| C1B-C2B-H2B2 | 106.3 | H2B1-C2B-H2B2 | 106.4 |
| C4B-C3B-C2B | 125.2(6) | C4B-C3B-H3B1 | 106.0 |
| C2B-C3B-H3B1 | 106.0 | C4B-C3B-H3B2 | 106.0 |
| C2B-C3B-H3B2 | 106.0 | H3B1-C3B-H3B2 | 106.3 |
| C3B-C4B-C5B | 125.2(6) | C3B-C4B-H4B1 | 106.0 |
| C5B-C4B-H4B1 | 106.0 | C3B-C4B-H4B2 | 106.0 |
| C5B-C4B-H4B2 | 106.0 | H4B1-C4B-H4B2 | 106.3 |
| C6B-C5B-C4B | 125.1(6) | C6B-C5B-H5B1 | 106.0 |
| C4B-C5B-H5B1 | 106.0 | C6B-C5B-H5B2 | 106.0 |
| C4B-C5B-H5B2 | 106.0 | H5B1-C5B-H5B2 | 106.3 |
| C5B-C6B-C7B | 125.3(6) | C5B-C6B-H6B1 | 106.0 |
| C7B-C6B-H6B1 | 106.0 | C5B-C6B-H6B2 | 106.0 |
| C7B-C6B-H6B2 | 106.0 | H6B1-C6B-H6B2 | 106.3 |
| C8B-C7B-C6B | 125.2(6) | C8B-C7B-H7B1 | 106.0 |
| C6B-C7B-H7B1 | 106.0 | C8B-C7B-H7B2 | 106.0 |
| C6B-C7B-H7B2 | 106.0 | H7B1-C7B-H7B2 | 106.3 |
| C9B-C8B-C7B | 125.1(6) | C9B-C8B-H8B1 | 106.0 |
| C7B-C8B-H8B1 | 106.0 | C9B-C8B-H8B2 | 106.0 |
| C7B-C8B-H8B2 | 106.0 | H8B1-C8B-H8B2 | 106.3 |
| C10B-C9B-C8B | 124.8(6) | C10B-C9B-H9B1 | 106.1 |
| C8B-C9B-H9B1 | 106.1 | C10B-C9B-H9B2 | 106.1 |
| C8B-C9B-H9B2 | 106.1 | H9B1-C9B-H9B2 | 106.3 |
| C9B-C10B-C11B | 125.7(6) | C9B-C10B-H10C | 105.9 |
| C11B-C10B-H10C | 105.9 | C9B-C10B-H10D | 105.9 |
| C11B-C10B-H10D | 105.9 | H10C-C10B-H10D | 106.2 |
| C12B-C11B-C10B | 124.0(6) | C12B-C11B-H11C | 106.3 |
| C10B-C11B-H11C | 106.3 | C12B-C11B-H11D | 106.3 |
| C10B-C11B-H11D | 106.3 | H11C-C11B-H11D | 106.4 |
| C11B-C12B-C13B | 126.1(6) | C11B-C12B-H12C | 105.8 |
| C13B-C12B-H12C | 105.8 | C11B-C12B-H12D | 105.8 |
| C13B-C12B-H12D | 105.8 | H12C-C12B-H12D | 106.2 |
| C14B-C13B-C12B | 124.8(6) | C14B-C13B-H13C | 106.1 |
| C12B-C13B-H13C | 106.1 | C14B-C13B-H13D | 106.1 |
| C12B-C13B-H13D | 106.1 | H13C-C13B-H13D | 106.3 |
| C15B-C14B-C13B | 130.9(6) | C15B-C14B-H14C | 104.5 |
| C13B-C14B-H14C | 104.5 | C15B-C14B-H14D | 104.5 |
| C13B-C14B-H14D | 104.5 | H14C-C14B-H14D | 105.7 |
| C14B-C15B-C16B | 117.5(5) | C14B-C15B-H15C | 107.9 |
| C16B-C15B-H15C | 107.9 | C14B-C15B-H15D | 107.9 |
| C16B-C15B-H15D | 107.9 | H15C-C15B-H15D | 107.2 |
| O1B-C16B-N1B | 123.8(4) | O1B-C16B-C15B | 120.8(5) |
| N1B-C16B-C15B | 115.4(4) | C16B-N1B-C17B | 122.4(4) |
| C16B-N1B-H1B | 118.8 | C17B-N1B-H1B | 118.8 |
| C18B-C17B-N1B | 118.3(5) | C18B-C17B-H17C | 107.7 |
| N1B-C17B-H17C | 107.7 | C18B-C17B-H17D | 107.7 |
| N1B-C17B-H17D | 107.7 | H17C-C17B-H17D | 107.1 |
| C17B-C18B-O2B | 119.8(6) | C17B-C18B-C19B | 122.1(5) |
| O2B-C18B-C19B | 106.1(5) | C17B-C18B-H18B | 101.7 |
| O2B-C18B-H18B | 101.7 | C19B-C18B-H18B | 101.7 |
| C18B-O2B-H2BA | 109.5 | O3B-C19B-C18B | 110.8(4) |
| O3B-C19B-H19C | 109.5 | C18B-C19B-H19C | 109.5 |
| O3B-C19B-H19D | 109.5 | C18B-C19B-H19D | 109.5 |

TABLE 5-continued

Torsion Angles

| Bond | Angle (°) | Bond | Angle (°) |
|---|---|---|---|
| H19C-C19B-H19D | 108.1 | C19B-O3B-C20B | 116.1(3) |
| O3B-C20B-C28B | 109.1(3) | O3B-C20B-C21B | 109.2(3) |
| C28B-C20B-C21B | 114.8(3) | O3B-C20B-C35B | 104.6(3) |
| C28B-C20B-C35B | 109.9(4) | C21B-C20B-C35B | 108.6(4) |
| C27B-C21B-C22B | 118.1(4) | C27B-C21B-C20B | 122.1(4) |
| C22B-C21B-C20B | 119.5(4) | C23B-C22B-C21B | 121.3(4) |
| C23B-C22B-H22B | 119.4 | C21B-C22B-H22B | 119.4 |
| C22B-C23B-C24B | 120.9(4) | C22B-C23B-H23B | 119.6 |
| C24B-C23B-H23B | 119.6 | O4B-C24B-C26B | 124.8(4) |
| O4B-C24B-C23B | 116.6(4) | C26B-C24B-C23B | 118.6(4) |
| C24B-O4B-C25B | 117.0(4) | O4B-C25B-H25D | 109.5 |
| O4B-C25B-H25E | 109.5 | H25D-C25B-H25E | 109.5 |
| O4B-C25B-H25F | 109.5 | H25D-C25B-H25F | 109.5 |
| H25E-C25B-H25F | 109.5 | C24B-C26B-C27B | 120.1(4) |
| C24B-C26B-H26B | 119.9 | C27B-C26B-H26B | 119.9 |
| C21B-C27B-C26B | 121.0(4) | C21B-C27B-H27B | 119.5 |
| C26B-C27B-H27B | 119.5 | C34B-C28B-C29B | 117.4(4) |
| C34B-C28B-C20B | 118.9(4) | C29B-C28B-C20B | 123.5(4) |
| C30B-C29B-C28B | 121.5(4) | C30B-C29B-H29B | 119.3 |
| C28B-C29B-H29B | 119.3 | C31B-C30B-C29B | 119.5(4) |

TABLE 5-continued

Torsion Angles

| Bond | Angle (°) | Bond | Angle (°) |
|---|---|---|---|
| C31B-C30B-H30B | 120.2 | C29B-C30B-H30B | 120.2 |
| O5B-C31B-C33B | 115.6(4) | O5B-C31B-C30B | 124.9(4) |
| C33B-C31B-C30B | 119.5(5) | C31B-O5B-C32B | 117.5(4) |
| O5B-C32B-H32D | 109.5 | O5B-C32B-H32E | 109.5 |
| H32D-C32B-H32E | 109.5 | O5B-C32B-H32F | 109.5 |
| H32D-C32B-H32F | 109.5 | H32E-C32B-H32F | 109.5 |
| C34B-C33B-C31B | 120.7(5) | C34B-C33B-H33B | 119.7 |
| C31B-C33B-H33B | 119.7 | C33B-C34B-C28B | 121.3(4) |
| C33B-C34B-H34B | 119.3 | C28B-C34B-H34B | 119.3 |
| C36B-C35B-C40B | 118.6(4) | C36B-C35B-C20B | 122.2(4) |
| C40B-C35B-C20B | 119.2(4) | C35B-C36B-C37B | 120.2(4) |
| C35B-C36B-H36B | 119.9 | C37B-C36B-H36B | 119.9 |
| C38B-C37B-C36B | 121.0(4) | C38B-C37B-H37B | 119.5 |
| C36B-C37B-H37B | 119.5 | C39B-C38B-C37B | 118.3(4) |
| C39B-C38B-H38B | 120.8 | C37B-C38B-H38B | 120.8 |
| C40B-C39B-C38B | 121.2(5) | C40B-C39B-H39B | 119.4 |
| C38B-C39B-H39B | 119.4 | C39B-C40B-C35B | 120.7(5) |
| C39B-C40B-H40B | 119.6 | C35B-C40B-H40B | 119.6 |

TABLE 6

Anisotropic Atomic Displacement Parameters

| | $U_{11}$ | $U_{22}$ | $U_{33}$ | $U_{23}$ | $U_{13}$ | $U_{12}$ |
|---|---|---|---|---|---|---|
| C1A | 0.096(6) | 0.093(6) | 0.091(6) | −0.063(5) | −0.002(5) | 0.014(5) |
| C2A | 0.061(4) | 0.060(4) | 0.069(4) | −0.036(3) | 0.001(3) | 0.000(3) |
| C3A | 0.051(3) | 0.058(4) | 0.059(4) | −0.029(3) | 0.003(3) | −0.001(3) |
| C4A | 0.053(3) | 0.053(4) | 0.059(4) | −0.025(3) | 0.012(3) | −0.010(3) |
| C5A | 0.055(4) | 0.058(4) | 0.064(4) | −0.033(3) | 0.009(3) | −0.010(3) |
| C6A | 0.060(4) | 0.055(4) | 0.057(4) | −0.026(3) | 0.013(3) | −0.013(3) |
| C7A | 0.059(4) | 0.053(4) | 0.064(4) | −0.029(3) | 0.009(3) | −0.017(3) |
| C8A | 0.055(4) | 0.055(4) | 0.063(4) | −0.028(3) | 0.014(3) | −0.014(3) |
| C9A | 0.063(4) | 0.051(4) | 0.057(4) | −0.027(3) | 0.010(3) | −0.009(3) |
| C10A | 0.065(4) | 0.050(3) | 0.055(4) | −0.025(3) | 0.019(3) | −0.017(3) |
| O1A | 0.0187(16) | 0.0336(18) | 0.069(2) | −0.0051(17) | 0.0063(15) | −0.0026(13) |
| N1A | 0.028(2) | 0.052(3) | 0.075(3) | −0.038(2) | 0.025(2) | −0.015(2) |
| C11A | 0.060(4) | 0.049(3) | 0.052(3) | −0.021(3) | 0.013(3) | −0.009(3) |
| C12A | 0.055(3) | 0.050(3) | 0.051(3) | −0.020(3) | 0.013(3) | −0.015(3) |
| C13A | 0.042(3) | 0.047(3) | 0.054(3) | −0.021(3) | 0.008(3) | −0.003(2) |
| C14A | 0.041(3) | 0.050(3) | 0.048(3) | −0.017(3) | 0.008(2) | −0.007(2) |
| C15A | 0.027(2) | 0.041(3) | 0.044(3) | −0.012(2) | 0.008(2) | −0.003(2) |
| C16A | 0.028(2) | 0.035(3) | 0.039(3) | −0.006(2) | 0.006(2) | −0.006(2) |
| C17A | 0.032(3) | 0.066(4) | 0.073(4) | −0.035(3) | 0.017(3) | −0.003(3) |
| C18A | 0.027(2) | 0.033(3) | 0.060(3) | −0.013(2) | 0.018(2) | −0.007(2) |
| O2A | 0.040(2) | 0.039(2) | 0.089(3) | −0.013(2) | 0.031(2) | −0.0074(17) |
| C19A | 0.025(2) | 0.026(2) | 0.051(3) | −0.009(2) | 0.018(2) | −0.0073(18) |
| O3A | 0.0236(15) | 0.0217(15) | 0.0463(19) | −0.0107(13) | 0.0141(13) | −0.0032(12) |
| C20A | 0.025(2) | 0.023(2) | 0.036(2) | −0.0083(18) | 0.0068(18) | −0.0006(17) |
| C21A | 0.022(2) | 0.023(2) | 0.034(2) | −0.0028(18) | 0.0071(18) | −0.0024(17) |
| C22A | 0.022(2) | 0.027(2) | 0.041(3) | 0.0004(19) | 0.0044(19) | 0.0009(18) |
| C23A | 0.028(2) | 0.037(3) | 0.036(3) | 0.005(2) | −0.003(2) | 0.001(2) |
| C24A | 0.029(2) | 0.034(3) | 0.026(2) | 0.0012(19) | 0.0032(18) | −0.0063(19) |
| O4A | 0.046(2) | 0.052(2) | 0.0313(18) | −0.0068(16) | −0.0056(15) | −0.0020(17) |
| C25A | 0.084(5) | 0.053(4) | 0.039(3) | −0.017(3) | −0.015(3) | −0.002(3) |
| C26A | 0.028(2) | 0.028(2) | 0.033(2) | −0.0081(19) | 0.0047(19) | 0.0006(18) |
| C27A | 0.022(2) | 0.027(2) | 0.030(2) | −0.0024(18) | −0.0011(17) | 0.0032(17) |
| C28A | 0.021(2) | 0.029(2) | 0.032(2) | −0.0105(19) | 0.0088(18) | −0.0020(17) |
| C29A | 0.030(2) | 0.029(2) | 0.038(3) | −0.008(2) | 0.003(2) | −0.0045(19) |
| C30A | 0.030(2) | 0.045(3) | 0.035(3) | −0.010(2) | −0.006(2) | −0.001(2) |
| C31A | 0.027(2) | 0.042(3) | 0.030(2) | −0.005(2) | 0.0037(19) | 0.006(2) |
| C32A | 0.079(4) | 0.047(3) | 0.040(3) | 0.005(3) | −0.007(3) | 0.006(3) |
| C33A | 0.032(2) | 0.032(3) | 0.033(3) | −0.004(2) | 0.003(2) | −0.0024(19) |
| O5A | 0.046(2) | 0.050(2) | 0.0347(19) | −0.0006(16) | −0.0027(16) | 0.0020(17) |
| C34A | 0.027(2) | 0.030(2) | 0.035(3) | −0.0077(19) | 0.0021(19) | −0.0034(18) |
| C35A | 0.024(2) | 0.025(2) | 0.032(2) | −0.0079(18) | 0.0023(18) | −0.0000(17) |
| C36A | 0.029(3) | 0.035(3) | 0.060(3) | −0.015(2) | 0.014(2) | −0.002(2) |
| C37A | 0.029(3) | 0.050(3) | 0.061(4) | −0.021(3) | 0.016(2) | −0.009(2) |
| C38A | 0.030(3) | 0.043(3) | 0.040(3) | −0.005(2) | 0.011(2) | −0.014(2) |
| C39A | 0.038(3) | 0.029(3) | 0.045(3) | −0.004(2) | 0.005(2) | −0.008(2) |
| C40A | 0.024(2) | 0.030(2) | 0.036(3) | −0.0054(19) | 0.0059(19) | −0.0001(18) |
| C1B | 0.074(5) | 0.069(5) | 0.073(5) | −0.027(4) | −0.009(4) | 0.013(4) |

TABLE 6-continued

| Anisotropic Atomic Displacement Parameters | | | | | | |
|---|---|---|---|---|---|---|
| | $U_{11}$ | $U_{22}$ | $U_{33}$ | $U_{23}$ | $U_{13}$ | $U_{12}$ |
| C2B | 0.087(6) | 0.088(6) | 0.111(7) | −0.064(5) | 0.050(5) | −0.026(4) |
| C3B | 0.062(4) | 0.074(5) | 0.075(5) | −0.033(4) | 0.018(3) | −0.014(3) |
| C4B | 0.054(4) | 0.066(4) | 0.077(5) | −0.034(4) | 0.022(3) | −0.014(3) |
| C5B | 0.080(5) | 0.081(5) | 0.095(6) | −0.048(4) | 0.050(4) | −0.038(4) |
| C6B | 0.051(4) | 0.062(4) | 0.069(4) | −0.025(3) | 0.016(3) | −0.011(3) |
| C7B | 0.092(6) | 0.095(6) | 0.104(6) | −0.065(5) | 0.059(5) | −0.052(5) |
| C8B | 0.062(4) | 0.066(4) | 0.067(4) | −0.027(3) | 0.024(3) | −0.014(3) |
| C9B | 0.094(6) | 0.084(5) | 0.101(6) | −0.058(5) | 0.060(5) | −0.052(4) |
| C10B | 0.071(4) | 0.063(4) | 0.071(4) | −0.029(4) | 0.026(4) | −0.013(3) |
| C11B | 0.079(5) | 0.074(5) | 0.090(5) | −0.040(4) | 0.046(4) | −0.028(4) |
| C12B | 0.087(5) | 0.069(5) | 0.075(5) | −0.032(4) | 0.041(4) | −0.026(4) |
| C13B | 0.057(4) | 0.062(4) | 0.061(4) | −0.022(3) | 0.021(3) | −0.014(3) |
| C14B | 0.173(9) | 0.057(4) | 0.091(6) | −0.032(4) | 0.091(6) | −0.056(5) |
| C15B | 0.076(4) | 0.035(3) | 0.047(3) | 0.001(2) | 0.020(3) | −0.011(3) |
| C16B | 0.027(2) | 0.019(2) | 0.045(3) | −0.0101(19) | 0.004(2) | −0.0028(18) |
| O1B | 0.0238(19) | 0.037(2) | 0.116(4) | −0.014(2) | 0.000(2) | 0.0026(15) |
| N1B | 0.0226(19) | 0.030(2) | 0.044(2) | 0.0049(17) | 0.0077(17) | 0.0046(16) |
| C17B | 0.095(5) | 0.040(3) | 0.070(4) | 0.012(3) | 0.055(4) | 0.013(3) |
| C18B | 0.057(4) | 0.033(3) | 0.155(7) | 0.031(4) | 0.076(5) | 0.025(3) |
| O2B | 0.035(2) | 0.034(2) | 0.083(3) | −0.0067(19) | 0.0280(19) | 0.0012(16) |
| C19B | 0.024(2) | 0.026(2) | 0.051(3) | −0.001(2) | 0.015(2) | 0.0051(18) |
| O3B | 0.0212(15) | 0.0211(15) | 0.050(2) | −0.0026(14) | 0.0151(14) | −0.0003(12) |
| C20B | 0.023(2) | 0.017(2) | 0.041(3) | −0.0001(18) | 0.0070(19) | 0.0008(17) |
| C21B | 0.021(2) | 0.021(2) | 0.039(3) | −0.0033(18) | 0.0079(18) | 0.0028(17) |
| C22B | 0.028(2) | 0.024(2) | 0.042(3) | −0.009(2) | 0.005(2) | −0.0010(18) |
| C23B | 0.028(2) | 0.042(3) | 0.038(3) | −0.014(2) | 0.000(2) | −0.003(2) |
| C24B | 0.029(2) | 0.034(3) | 0.028(2) | −0.0048(19) | 0.0067(19) | 0.0033(19) |
| O4B | 0.042(2) | 0.044(2) | 0.0313(18) | 0.0009(15) | −0.0040(15) | 0.0037(16) |
| C25B | 0.090(5) | 0.041(3) | 0.046(3) | 0.004(3) | −0.018(3) | 0.001(3) |
| C26B | 0.030(2) | 0.026(2) | 0.037(3) | −0.0024(19) | 0.0051(19) | −0.0003(18) |
| C27B | 0.021(2) | 0.028(2) | 0.036(2) | −0.0025(19) | −0.0014(18) | 0.0000(17) |
| C28B | 0.025(2) | 0.021(2) | 0.035(2) | −0.0009(18) | 0.0087(18) | −0.0004(17) |
| C29B | 0.026(2) | 0.031(2) | 0.038(3) | −0.002(2) | 0.0004(19) | 0.0031(19) |
| C30B | 0.033(3) | 0.027(2) | 0.043(3) | −0.004(2) | 0.008(2) | 0.0025(19) |
| C31B | 0.033(3) | 0.035(3) | 0.038(3) | −0.004(2) | 0.006(2) | −0.006(2) |
| O5B | 0.047(2) | 0.052(2) | 0.048(2) | −0.0158(18) | −0.0064(17) | 0.0074(18) |
| C32B | 0.082(5) | 0.045(3) | 0.047(3) | −0.015(3) | 0.000(3) | −0.003(3) |
| C33B | 0.031(3) | 0.042(3) | 0.043(3) | −0.001(2) | −0.005(2) | 0.008(2) |
| C34B | 0.036(3) | 0.026(2) | 0.042(3) | −0.004(2) | 0.005(2) | 0.004(2) |
| C35B | 0.024(2) | 0.026(2) | 0.034(2) | −0.0019(19) | 0.0055(18) | 0.0015(18) |
| C36B | 0.026(2) | 0.024(2) | 0.041(3) | −0.0020(19) | 0.0058(19) | 0.0013(18) |
| C37B | 0.034(3) | 0.025(2) | 0.055(3) | −0.010(2) | 0.003(2) | 0.007(2) |
| C38B | 0.034(3) | 0.041(3) | 0.046(3) | −0.002(2) | 0.010(2) | 0.016(2) |
| C39B | 0.034(3) | 0.046(3) | 0.060(4) | 0.006(3) | 0.025(3) | 0.004(2) |
| C40B | 0.032(3) | 0.026(2) | 0.060(3) | 0.001(2) | 0.016(2) | 0.001(2) |

TABLE 7

| Hydrogen atomic coordinates and isotropic atomic displacement parameters | | | | |
|---|---|---|---|---|
| | x/a | y/b | z/c | U(eq) |
| H1AA | 1.2927 | −0.2579 | 0.3388 | 0.134 |
| H1AB | 1.3853 | −0.2887 | 0.3796 | 0.134 |
| H1AC | 1.4410 | −0.1919 | 0.3478 | 0.134 |
| H2AA | 1.1632 | −0.2008 | 0.3976 | 0.074 |
| H2AB | 1.2048 | −0.1066 | 0.3631 | 0.074 |
| H3AA | 1.3749 | −0.1576 | 0.4355 | 0.066 |
| H3AB | 1.4212 | −0.0651 | 0.4006 | 0.066 |
| H4AA | 1.1439 | −0.0713 | 0.4513 | 0.065 |
| H4AB | 1.1857 | 0.0201 | 0.4157 | 0.065 |
| H5AA | 1.3544 | −0.0229 | 0.4889 | 0.069 |
| H5AB | 1.3999 | 0.0673 | 0.4530 | 0.069 |
| H6AA | 1.1177 | 0.0627 | 0.5018 | 0.067 |
| H6AB | 1.1649 | 0.1532 | 0.4662 | 0.067 |
| H7AA | 1.3221 | 0.1115 | 0.5414 | 0.069 |
| H7AB | 1.3723 | 0.2011 | 0.5056 | 0.069 |
| H8AA | 1.1351 | 0.2870 | 0.5161 | 0.068 |
| H8AB | 1.0841 | 0.1973 | 0.5516 | 0.068 |
| H9AA | 1.3348 | 0.3372 | 0.5570 | 0.067 |
| H9AB | 1.2834 | 0.2475 | 0.5925 | 0.067 |
| H10A | 1.0964 | 0.4221 | 0.5664 | 0.067 |

TABLE 7-continued

| Hydrogen atomic coordinates and isotropic atomic displacement parameters | | | | |
|---|---|---|---|---|
| | x/a | y/b | z/c | U(eq) |
| H10B | 1.0439 | 0.3322 | 0.6016 | 0.067 |
| H1A | 1.1384 | 0.8576 | 0.7529 | 0.06 |
| H11A | 1.2922 | 0.4724 | 0.6082 | 0.064 |
| H11B | 1.2383 | 0.3829 | 0.6435 | 0.064 |
| H12A | 0.9961 | 0.4676 | 0.6500 | 0.062 |
| H12B | 1.0562 | 0.5587 | 0.6161 | 0.062 |
| H13A | 1.1838 | 0.5127 | 0.6951 | 0.057 |
| H13B | 1.2474 | 0.6025 | 0.6612 | 0.057 |
| H14A | 0.9443 | 0.6043 | 0.6988 | 0.055 |
| H14B | 1.0189 | 0.6966 | 0.6676 | 0.055 |
| H15A | 1.1470 | 0.6322 | 0.7457 | 0.045 |
| H15B | 1.1973 | 0.7335 | 0.7155 | 0.045 |
| H17A | 0.8911 | 0.9614 | 0.7580 | 0.067 |
| H17B | 0.8581 | 0.8735 | 0.7958 | 0.067 |
| H18A | 1.0716 | 0.9254 | 0.8284 | 0.048 |
| H2A | 1.2212 | 0.9921 | 0.7785 | 0.084 |
| H19A | 0.9846 | 1.0877 | 0.8449 | 0.042 |
| H19B | 0.8955 | 1.1078 | 0.8027 | 0.042 |
| H22A | 0.8846 | 1.0003 | 0.9134 | 0.036 |
| H23A | 0.9700 | 1.0632 | 0.9722 | 0.041 |

TABLE 7-continued

| Hydrogen atomic coordinates and isotropic atomic displacement parameters | | | | |
|---|---|---|---|---|
| | x/a | y/b | z/c | U(eq) |
| H25A | 0.8974 | 1.3835 | 0.9890 | 0.086 |
| H25B | 0.9194 | 1.3455 | 1.0366 | 0.086 |
| H25C | 0.7551 | 1.3340 | 1.0172 | 0.086 |
| H26A | 0.7013 | 1.3166 | 0.9514 | 0.035 |
| H27A | 0.6095 | 1.2515 | 0.8932 | 0.032 |
| H29A | 0.4915 | 1.0342 | 0.8014 | 0.039 |
| H30A | 0.4180 | 1.1336 | 0.7421 | 0.043 |
| H32A | 0.6439 | 1.4191 | 0.7036 | 0.084 |
| H32B | 0.5009 | 1.4676 | 0.7274 | 0.084 |
| H32C | 0.4902 | 1.4499 | 0.6799 | 0.084 |
| H33A | 0.6524 | 1.3797 | 0.7748 | 0.039 |
| H34A | 0.7409 | 1.2743 | 0.8317 | 0.037 |
| H36A | 0.4098 | 1.1154 | 0.8957 | 0.049 |
| H37A | 0.1989 | 1.0139 | 0.9210 | 0.056 |
| H38A | 0.2069 | 0.8328 | 0.9200 | 0.046 |
| H39A | 0.4223 | 0.7577 | 0.8904 | 0.045 |
| H40A | 0.6314 | 0.8599 | 0.8635 | 0.036 |
| H1BA | 0.8569 | −0.0205 | 0.3248 | 0.106 |
| H1BB | 0.7153 | −0.0378 | 0.3579 | 0.106 |
| H1BC | 0.8838 | −0.0772 | 0.3699 | 0.106 |
| H2B1 | 0.9713 | 0.0814 | 0.3698 | 0.112 |
| H2B2 | 0.8281 | 0.1304 | 0.3462 | 0.112 |
| H3B1 | 0.6812 | 0.1040 | 0.4048 | 0.083 |
| H3B2 | 0.8243 | 0.0551 | 0.4282 | 0.083 |
| H4B1 | 0.7958 | 0.2605 | 0.3988 | 0.077 |
| H4B2 | 0.9371 | 0.2110 | 0.4230 | 0.077 |
| H5B1 | 0.6450 | 0.2338 | 0.4572 | 0.101 |
| H5B2 | 0.7880 | 0.1865 | 0.4812 | 0.101 |
| H6B1 | 0.7589 | 0.3911 | 0.4507 | 0.072 |
| H6B2 | 0.8985 | 0.3429 | 0.4758 | 0.072 |
| H7B1 | 0.6043 | 0.3658 | 0.5084 | 0.114 |
| H7B2 | 0.7464 | 0.3205 | 0.5333 | 0.114 |
| H8B1 | 0.8552 | 0.4801 | 0.5262 | 0.077 |
| H8B2 | 0.7113 | 0.5249 | 0.5019 | 0.077 |
| H9B1 | 0.5628 | 0.4977 | 0.5605 | 0.109 |
| H9B2 | 0.7087 | 0.4556 | 0.5845 | 0.109 |
| H10C | 0.6651 | 0.6572 | 0.5522 | 0.081 |
| H10D | 0.8113 | 0.6152 | 0.5761 | 0.081 |
| H11C | 0.5194 | 0.6338 | 0.6116 | 0.096 |
| H11D | 0.6660 | 0.5921 | 0.6355 | 0.096 |
| H12C | 0.6183 | 0.7928 | 0.6023 | 0.092 |
| H12D | 0.7709 | 0.7531 | 0.6236 | 0.092 |
| H13C | 0.4900 | 0.7663 | 0.6644 | 0.071 |
| H13D | 0.6480 | 0.7343 | 0.6847 | 0.071 |
| H14C | 0.7288 | 0.9024 | 0.6631 | 0.13 |
| H14D | 0.5552 | 0.9265 | 0.6534 | 0.13 |
| H15C | 0.5629 | 0.9980 | 0.7042 | 0.064 |
| H15D | 0.7020 | 0.9295 | 0.7223 | 0.064 |
| H1B | 0.6496 | 0.7808 | 0.7640 | 0.04 |
| H17C | 0.4194 | 0.7514 | 0.8162 | 0.085 |
| H17D | 0.3617 | 0.7014 | 0.7771 | 0.085 |
| H18B | 0.5819 | 0.6437 | 0.8289 | 0.105 |
| H2BA | 0.715(7) | 0.626(4) | 0.7726(18) | 0.078 |
| H19C | 0.3934 | 0.4909 | 0.8077 | 0.041 |
| H19D | 0.4882 | 0.4974 | 0.8483 | 0.041 |
| H22B | 0.3819 | 0.5391 | 0.9188 | 0.037 |
| H23B | 0.4737 | 0.4403 | 0.9754 | 0.043 |
| H25D | 0.2741 | 0.1374 | 1.0191 | 0.088 |
| H25E | 0.4476 | 0.1152 | 1.0321 | 0.088 |
| H25F | 0.4039 | 0.1137 | 0.9851 | 0.088 |

TABLE 7-continued

| Hydrogen atomic coordinates and isotropic atomic displacement parameters | | | | |
|---|---|---|---|---|
| | x/a | y/b | z/c | U(eq) |
| H26B | 0.2100 | 0.1981 | 0.9519 | 0.037 |
| H27B | 0.1129 | 0.3005 | 0.8955 | 0.034 |
| H29B | 0.2688 | 0.3208 | 0.8325 | 0.038 |
| H30B | 0.1874 | 0.2456 | 0.7751 | 0.042 |
| H32D | 0.0040 | 0.2183 | 0.6833 | 0.086 |
| H32E | 0.0351 | 0.1730 | 0.7297 | 0.086 |
| H32F | 0.1594 | 0.2481 | 0.7040 | 0.086 |
| H33B | −0.1223 | 0.4768 | 0.7547 | 0.047 |
| H34B | −0.0483 | 0.5478 | 0.8128 | 0.042 |
| H36B | 0.1210 | 0.7079 | 0.8592 | 0.037 |
| H37B | −0.0863 | 0.7996 | 0.8853 | 0.045 |
| H38B | −0.2897 | 0.7119 | 0.9234 | 0.049 |
| H39B | −0.2830 | 0.5308 | 0.9347 | 0.058 |
| H40B | −0.0782 | 0.4390 | 0.9091 | 0.049 |

What is claimed is:

1. A crystalline solid of a compound of Formula II (II)

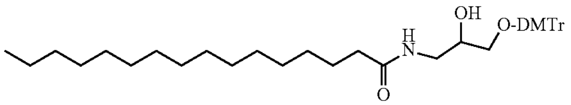

wherein DMTr is dimethoxytriphenylmethyl;

each unit cell in the crystalline solid comprises conformer A and conformer B of the compound of Formula II; and conformer A has the atomic coordinates and equivalent isotropic displacement parameters:

| | | | | |
|---|---|---|---|---|
| O1A | 0.8579(3) | 0.7210(3) | 0.75600(12) | 0.0408(9) |
| N1A | 0.0410(5) | 0.8405(4) | 0.75844(15) | 0.0504(13). |

2. The crystalline solid of claim 1, wherein conformer B has the atomic coordinates and equivalent isotropic displacement parameters:

| | | | | |
|---|---|---|---|---|
| O1B | 0.3551(4) | 0.8951(3) | 0.74538(15) | 0.0585(12) |
| N1B | 0.5490(4) | 0.7896(3) | 0.76518(12) | 0.0331(9). |

3. The crystalline solid of claim 1, wherein conformer A has the atomic coordinates and equivalent isotropic displacement parameters set forth in Table 2.

4. The crystalline solid of claim 1, wherein conformer B has the atomic coordinates and equivalent isotropic displacement parameters set forth in Table 2.

* * * * *